United States Patent
Wagtmann et al.

(10) Patent No.: US 9,879,082 B2
(45) Date of Patent: *Jan. 30, 2018

(54) ANTI-KIR ANTIBODIES, FORMULATIONS, AND USES THEREOF

(71) Applicant: NOVO NORDISK A/S, Bagsvaerd (DE)

(72) Inventors: Peter Andreas Nicolai Reumert Wagtmann, Rungsted Kyst (DE); Ivan Svendsen, Smorum (DE); Rozana Sten, Malmo (SE); Lene Hjorth Alifrangis, Viby (DE); Rune Viig Overgaard, Copenhagen (DE)

(73) Assignee: NOVO NORDISK A/S, Bagsvaerd (DE)

( * ) Notice: Subject to any disclaimer, the term of this patent is extended or adjusted under 35 U.S.C. 154(b) by 351 days.

This patent is subject to a terminal disclaimer.

(21) Appl. No.: 14/606,814

(22) Filed: Jan. 27, 2015

(65) Prior Publication Data

US 2015/0197569 A1    Jul. 16, 2015

Related U.S. Application Data

(63) Continuation of application No. 12/521,105, filed as application No. PCT/EP2008/050306 on Jan. 11, 2008, now abandoned.

(60) Provisional application No. 60/911,527, filed on Apr. 13, 2007, provisional application No. 60/879,964, filed on Jan. 11, 2007.

(51) Int. Cl.
| | | |
|---|---|---|
| C07K 16/00 | (2006.01) | |
| C12P 21/08 | (2006.01) | |
| C07K 16/28 | (2006.01) | |
| A61K 39/395 | (2006.01) | |
| A61K 39/00 | (2006.01) | |

(52) U.S. Cl.
CPC .......... *C07K 16/28* (2013.01); *A61K 39/3955* (2013.01); *A61K 39/39541* (2013.01); *C07K 16/2803* (2013.01); *A61K 2039/505* (2013.01); *A61K 2039/545* (2013.01)

(58) Field of Classification Search
None
See application file for complete search history.

(56) References Cited

U.S. PATENT DOCUMENTS

| | | | | |
|---|---|---|---|---|
| 8,709,411 | B2* | 4/2014 | Farag | A61K 31/4439 |
| | | | | 424/130.1 |
| 9,067,997 | B2* | 6/2015 | Romagne | C07K 16/2803 |
| 9,415,104 | B2* | 8/2016 | Farag | A61K 31/4439 |
| 2004/0152632 | A1 | 8/2004 | Feinfold et al. | |
| 2005/0255118 | A1 | 11/2005 | Wehner | |
| 2006/0280740 | A1 | 12/2006 | Padkjaer et al. | |

FOREIGN PATENT DOCUMENTS

| | | |
|---|---|---|
| JP | 2005518802 A | 6/2005 |
| JP | 2005526956 A | 9/2005 |
| WO | WO 1995/026403 | 10/1995 |
| WO | WO 2001/078779 | 10/2001 |
| WO | WO 2003/016468 | 2/2003 |
| WO | 2003054517 A2 | 7/2003 |
| WO | 2003073982 A2 | 9/2003 |
| WO | WO 2005/003168 | 1/2005 |
| WO | WO 2005/003172 | 1/2005 |
| WO | 2005068503 A2 | 7/2005 |
| WO | WO 2006/003179 | 1/2006 |
| WO | WO 2006/072626 | 7/2006 |
| WO | WO 2006/116369 | 11/2006 |

OTHER PUBLICATIONS

Aalberse RC, et al. "IgG4 breaking the rules," Immunology. Jan. 2002;105(1):9-19.
Forrer K, et al. "Chip-based gel electrophoresis method for the quantification of half-antibody species in IgG4 and their by- and degradation products," Anal Biochem. Nov. 1, 2004;334(1):81-8.
Peters SJ, et al. "Engineering an improved IgG4 molecule with reduced disulfide bond heterogeneity and increased Fab domain thermal stability," J Biol Chem. Jul. 13, 2012;287(29):24525-33.
Beerli RR, et al. "Mining human antibody repertoires," MAbs. Jul.-Aug. 2010;2(4):365-78.
Vey, et al. "A phase 1 trial of the anti-inhibitory KIR mAb IPH2101 for AML in complete remission," Blood. Nov. 22, 2012;120(22):4317-23. Supplemental data.
Angal, S. et al., "A single amino acid substitution abolishes the heterogeneity of chimeric mouse/human (IgG4) antibody," Molecular Immunology, vol. 30, Issue 1, Jan. 1993, pp. 105-108.
Bloom J. W. et al., "Intrachain disulfide bond in the core hinge region of human IgG4," Protein Science, 6: 407-415.
Schuurman J., et al., "The inter-heavy chain disulfide bonds of IgG4 are in equilibrium with intra-chain disulfide bonds," Molecular Immunology, vol. 38, Issue 1, Jan. 2001, pp. 1-8.
Campbell KS, et al. "Structure/function of human killer cell immunoglobulin-like receptors: lessons from polymorphisms, evolution, crystal structures and mutations," Immunology. Mar. 2011;132(3):315-25.

(Continued)

*Primary Examiner* — Amy Juedes
(74) *Attorney, Agent, or Firm* — Robin L. Teskin; LeClairRyan, A Professional Corporation

(57) ABSTRACT

A novel IgG4 isotype anti-KIR antibody, novel formulations of this and other IgG4 anti-KIR antibodies, and methods of using such formulations are provided. Also described are compositions, formulations, dosages, and administration regimens suitable for NK cell activation and therapeutic applications of anti-KIR antibodies, as well as kits comprising one or more anti-KIR antibodies with instructions for use in treating cancer.

12 Claims, 16 Drawing Sheets

(56) References Cited

OTHER PUBLICATIONS

Ghielmini M. "Multimodality therapies and optimal schedule of antibodies: rituximab in lymphoma as an example," Hematology Am Soc Hematol Educ Program. 2005:321-8.

Solèr M., et al. "The anti-IgE antibody omalizumab reduces exacerbations and steroid requirement in allergic asthmatics," Eur Respir J. Aug. 2001;18(2):254-61.

Alter, G. et al. "CD107a as a functional marker for the identification of natural killer cell activity," Journal of Immunological Methods, 2004, pp. 15-22, vol. 294, XP-004679751.

Wang, W. et al. "Antibody Structure, Instability, and Formulation," Journal of Pharmaceutical Sciences, Jan. 2007, pp. 1-26, vol. 96, No. 1, XP-009084505.

Daugherty, A. L. et al. "Formulation and delivery issues for monoclonal antibody therapeutics" Advanced Drug Delivery Reviews, 2006, pp. 686-706, vol. 58, No. 5-6, XP-005611422.

Koh, C. Y. et al. "Augmentation of antitumor effects by NK cell inhibitory receptor blockade in vitro and in vivo," Blood, May 15, 2001, pp, 3132-3137, vol. 97, No. 10, XP-002308582.

Mould, D.R. et al. "The pharmacokinetics and pharmacodynamics of monoclonal antibodies—mechanistic modeling applied to drug development" Current Opinion in Drug Discovery & Development, Jan. 2007, pp. 84-96, vol. 10, No. 1, XP-009097022.

Sheiner, L. B. et al. "Pharmacokinetic/Pharmacodynamic Modeling in Drug Development," Annu. Rev. Pharmacology Toxicology, 2000, pp. 67-95, vol. 40, XP002472430.

Lobo, E.D. et al. "Antibody Pharmacokinetics and Pharmacodynamics" Journal of Pharmaceutical Sciences, Nov. 2004, pp. 2645-2648, vol. 93, No. 11, XP008070609.

* cited by examiner

MDWTWRFLFVVAASTGVQSQVQLVQSGAEVKKPGSSVKVSCKASGGTFSFYAISWVRQAPGQ
GLEWMGGFIPIFGAANYAQKFQGRVTITADESTSTAYMELSSLRSDDTAVYYCARIPSGSYY
YDYDMDVWGQGTTVTVSSASTKGPSVFPLAPCSRSTSESTAALGCLVKDYFPEPVTVSWNSG
ALTSGVHTFPAVLQSSGLYSLSSVVTVPSSSLGTKTYTCNVDHKPSNTKVDKRVESKYGPPC
PPCPAPEFLGGPSVFLFPPKPKDTLMISRTPEVTCVVVDVSQEDPEVQFNWYVDGVEVHNAK
TKPREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK*

Fig. 1

Overall results for sample 1 :     <u>anti-kir OP004 SCH513</u>
Number of peaks found:     3
Total Rel Conc:     672.2 µg/ml
Peak table for sample 1 :     <u>anti-kir OP004 SCH513</u>

| Peak | Size [kDa] | Rel. Conc. | Calib. Conc. | %total | Observations |
|---|---|---|---|---|---|
| 1 | 4.5 | 0.0 | 0.0 | 0.0 | Lower marker |
| 2 | 7.0 | 0.0 | 0.0 | 0.0 | System peak |
| 3 | 82.8 | 29.4 | 0.0 | 4.4 | |
| 4 | 132.7 | 7.3 | 0.0 | 1.1 | |
| 5 | 149.8 | 635.4 | 0.0 | 94.5 | |
| 6 | 240.0 | 60.0 | 0.0 | 0.0 | Upper marker |

Overall results for sample 2: <u>SCH778 pool 1+2</u>
Number of peaks found: 2
Total Rel Conc: 1,319.3 µg/ml
Peak table for sample 12: <u>SCH778 pool 1+2</u>

| Peak | Size [kDa] | Rel. Conc. | Calib. Conc. | %total | Observations |
|---|---|---|---|---|---|
| 1 | 4.5 | 0.0 | 0.0 | 0.0 | Lower marker |
| 2 | 7.5 | 0.0 | 0.0 | 0.0 | System peak |
| 3 | 131.9 | 8.8 | 0.0 | 0.7 | |
| 4 | 148.2 | 1,310.5 | 0.0 | 99.3 | |
| 5 | 240.0 | 60.0 | 0.0 | 0.0 | Upper marker |

US 9,879,082 B2

ANTI-KIR ANTIBODIES, FORMULATIONS, AND USES THEREOF

This application is a continuation of U.S. application Ser. No. 12/521,105 filed Jan. 15, 2010, which is a U.S. 371 application of international application PCT/EP08/50306 filed Jan. 11, 2008 (published as WO 2008/084106) which claims priority to U.S. Provisional Application 60/911,527 filed Apr. 13, 2007 and U.S. Provisional Application 60/879,964 filed Jan. 11, 2007, the disclosure of all of which listed above are herein incorporated by reference in their entirety.

FIELD OF THE INVENTION

This invention relates to novel antibodies against certain Killer Immunoglobulin-like Receptors (KIRs); formulations, dosages, and administration schedules for these and/or other therapeutic anti-KIR antibodies; and methods of producing and using the same.

SEQUENCE LISTING DISCLOSURE

This application includes as part of its disclosure a biological sequence listing contained in a file named "43271o3202.txt" having a size of 10,768 bytes that was created Jan. 27, 2015, which is hereby incorporated by reference in its entirety.

BACKGROUND OF THE INVENTION

KIRs are polymorphic type 1 trans-membrane molecules present on certain subsets of lymphocytes, including NK cells and some T cells. KIRs interact with determinants in the alpha 1 and 2 domains of MHC class I molecules. In patients with AML, haplo-identical stem cell transplantation (SCT) can lead to expansion and activation of KIR-HLA class I mismatched NK cells, resulting in reduced rates of leukemia relapse, no graft-versus-host disease, and markedly improved survival rates (Ruggeri et al., Science 2002; 295:2029-31). The molecular basis for the clinical efficacy of haplo-identical SCT is that NK cell-mediated tumor killing is regulated by inhibitory KIR receptors. Upon binding to their specific HLA-B or -C ligands, these NK cell receptors transmit negative signals which inhibit NK cell-mediated killing of tumors. As HLA-B and -C molecules are highly polymorphic in the population, and distinct HLA allotypes are recognized by either KIR2DL1 or by KIR2DL2/3, it is often possible to find donors and recipients who KIR and HLA are mismatched, i.e., where the KIR of the donor do not bind an HLA ligand in the recipient. In such situations, there is no transmission of inhibitory signals via the KIR that fail to bind HLA ligands, facilitating activation of NK cells. However, this SCT protocol is not available to all patients, e.g., to the majority of AML patients who are elderly.

To achieve similar NK-mediated anti-leukemia activity by a pharmacological approach, a humanized or fully human anti-KIR antibody that is capable of blocking inhibitory KIR signalling can be used. Anti-KIR antibodies having advantageous pharmacological properties and useful in, e.g., the treatment of cancer or infectious diseases are described in WO2006003179, WO2006072626, WO2005003172, and WO2005003168. However, for clinical applications of such antibodies, optimized formulations and effective administration regimens are needed.

The invention described herein concerns formulations and administration regimens for anti-KIR antibodies, suitable for their use in promoting physiological effects useful in the treatment of cancer and other disorders or diseases.

SUMMARY OF THE INVENTION

The present invention provides compositions of anti-KIR antibodies which, when administered, modulate NK cell activity in vivo. When used in particular dosage regimens, these compositions lead to efficient occupancy of KIR receptors on NK cells, and are useful in treating e.g., cancer and viral diseases.

Provides are also S241P variant of anti-KIR antibody 1-7F9 (described in WO2006003179), novel pharmaceutical formulations that can be used with the variant and/or 1-7F9, methods of producing the same, and methods of using these compositions for promoting physiological effects, such as in the treatment of cancer and viral diseases.

DESCRIPTION OF THE DRAWINGS

FIG. 1 shows the amino acid sequence of the mutated heavy chain encoding an S241P variant of Anti-KIR(1-7F9) (SEQ ID NO:1), with the mutated proline residue in bold.

DESCRIPTION OF THE INVENTION

Figure 2:
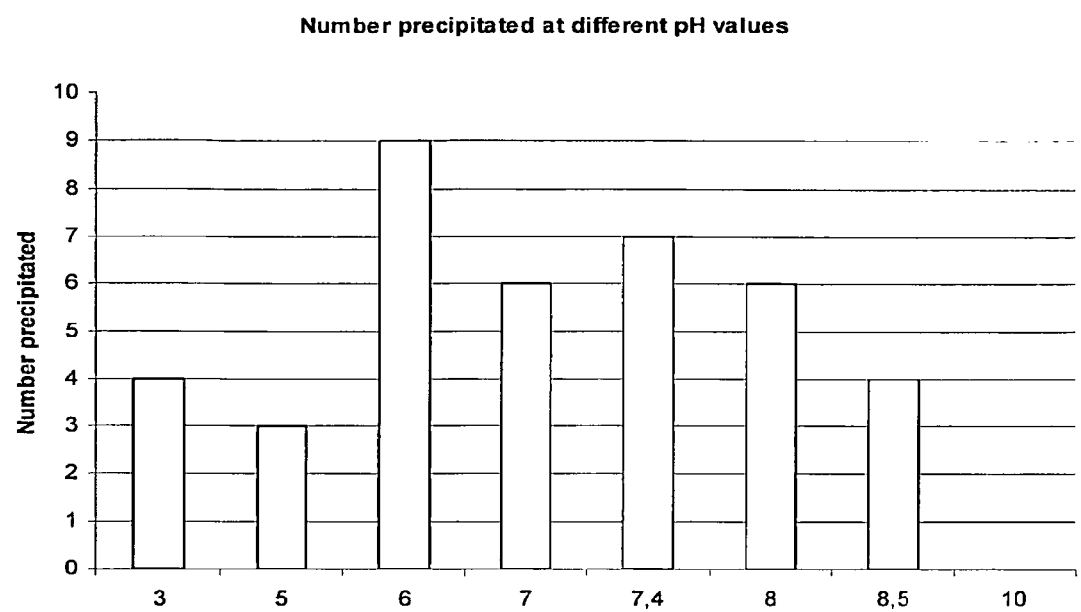
FIG. 2 shows the results from a pH solubility study of Anti-KIR(1-7F9).

As described above, the present invention provides compositions, formulations, dosages, and administration regimens suitable for NK cell activation and therapeutic applications of anti-KIR antibodies, as well as kits comprising one or more anti-KIR antibodies with instructions for use in treating cancer or a viral disease.

In one aspect, the invention provides an anti-KIR antibody administration regimen characterized by the exemplary dose-dosage regimen (or dosing frequency) combinations described in Table 1.

TABLE 1

Doses and dosage regimens for an anti-KIR antibody

| Dose (mg/kg) | Dosing regimen |
|---|---|
| 0.003 | 1-2 times per day |
| 0.015 | 3-5 times per week |
| 0.075 | 1-2 times per week |
| 0.3 | 1-2 times per month |
| 1 | About 1 time per month |
| 3 | 1-2 times per 2-month period |

The specific values described in Table 1 should be understood to be approximate. For example, for each dose-dosage regimen in Table 1, efficient NK cell modulation may also be achieved by administering a higher dose at the same dosing frequency, or by administering the same dose at a higher dosing frequency.

The administration regimens provided are based, in part, on a combination of PK/PD modelling and data from patient studies on anti-KIR antibody 1-7F9, as described in the Examples. Without being bound by theory, the administration regimens in Table 1 lead to efficient NK cell modulation by achieving high KIR occupancy levels, such as at least about 90%, or at least about 95%, on NK cells in blood after administration of an anti-KIR antibody to a human patient. Other anti-KIR antibodies having suitable properties for obtaining similarly high occupancy levels can also be used in an administration regimen according to the invention, as described herein.

In the clinical setting of haplo-identical SCT between KIR and HLA mismatched donors and recipients, it is possible to detect donor-derived NK cells in the circulation of patients for up to about 3 months after transplantation; nevertheless, it is possible that the NK cells persist for considerably longer, but in quantities that preclude their identification in blood. It should be noted that every individual expresses a repertoire of different KIRs that are clonally distributed on NK cells, and even in a haplo-identical SCT setting, only a subset of donor-derived NK cells will express specific KIRs that fail to bind HLA in the recipient. Hence, complete lack of signalling via a subset of specific KIRs, on a subset of NK cells, for at least three months, is sufficient to achieve significant clinical benefit.

Based on these premises, a therapeutically effective dosing schedule of a neutralizing anti-KIR antibody is one that results in a sufficiently high (e.g., full or near-full) blocking of the KIR receptors for a period of at least about three months, preferably for at least 6 months. However, until now, it has not been known if sufficiently high blockage could be achieved in human patients, or what doses of an anti-KIR antibodies were required to achieve such blockage. Surprisingly, as described herein, low doses of Anti-KIR(1-7F9) were sufficient to (ii) detectably activate NK-cell mediated killing of tumor cells in vivo, and (i) to achieve a near-full receptor blockade, in patients. Although full-length human or humanized antibodies typically have a long half-life in blood, to achieve full or near-full KIR occupancy for several months, it is necessary to give repeated administrations at some defined interval. From a combination of PK/PD modelling and human clinical data, it has now been revealed what administration regimens can achieve continuous KIR blockade (see Table 1 and Example 12).

In another aspect, the invention provides formulations suitable for 1-7F9, 1-7F9(S241P), or similar IgG4 antibodies, particularly similar anti-KIR IgG4 antibodies and/or cross-reactive anti-KIR antibodies. The formulations described herein have been determined to be associated with advantageous pharmacological properties including (a) a low level of antibody molecule precipitation (suitable solubility and low levels of particle formation), (b) an acceptable level of antibody molecule stability (in terms of maintenance of monomeric structure and secondary structural elements), and (c) a low level of aggregation formation.

Anti-KIR Antibodies

Anti-KIR antibodies useful in the present invention are NK cell-modulatory, i.e., effective in modulating NK cell activity, typically by reducing KIR signalling. This can be achieved either by the antibody blocking HLA-ligand from binding to a KIR molecule, or by a non-competitive antagonist mechanism of the antibody (see WO2006072626). For an anti-KIR antibody reducing or blocking the signalling of one or more inhibitory KIRs such as, e.g., KIR2DL1, KIR2DL2, and KIR2DL3, herein called "a neutralizing anti-KIR antibody", a high KIR occupancy leads to potentiation of NK cell activity. Suitable anti-KIR antibodies may also either be mono-specific, i.e., bind to a single type of KIR-molecule, or multi-specific, i.e., bind to more than one KIR molecule. An anti-KIR antibody binding at least to all of KIR2DL1, KIR2DL2, and KIR2DL3 is herein called "a cross-reactive antibody." Exemplary antibodies of useful for applications according to the invention include those described in WO2006003179 and WO2006072626. For example, neutralizing and cross-reactive anti-KIR antibody 1-7F9 (also called "Anti-KIR(1-7F9)", "1-7F9", and "Anti-KIR") blocks the interactions of inhibitory KIR2DL receptors KIR2DL1, KIR2DL2, and KIR2DL3 with their HLA-C ligands, thereby enhancing NK cell cytotoxic activity. As described in Examples 13 and 14, even single, low doses of 1-7F9 were capable of reducing tumor markers in most patients tested so far in dose-escalation trials conducted in patients suffering from AML or multiple myeloma. The variable light and heavy chain sequences of Anti-KIR(1-7F9) are set forth in SEQ ID NO:2 and SEQ ID NO:3, respectively.

However, the invention also provides a novel variant of the anti-KIR IgG4 antibody 1-7F9. The variant provided comprises an IgG4 heavy chain comprising the 1-7F9 variable heavy chain sequence and a serine to proline mutation in residue 241, corresponding to position 228 according to the EU-index (Kabat et al., "Sequences of proteins of immunological interest", 5$^{th}$ ed., NIH, Bethesda, Md., 1991). Also provided are 1-7F9 variants of IgG4 isotype comprising a heavy chain according to SEQ ID NO:1 provided herein. The nucleotide sequence encoding SEQ ID NO:1 is set forth in SEQ ID NO:6, and its complementary sequence is set forth in SEQ ID NO:7. The variant can further comprise a light chain that comprises a light chain variable region according to SEQ ID NO:2. This variant is also referred to as 1-7F9(S241P). Typically, the antibody variant is expressed recombinantly in CHO cells or another suitable cell type. As shown in the Examples, the mutation does not interfere with the ability of the variant antibody to bind to KIR antigens bound by 1-7F9. As such, the 1-7F9 (S241P) antibody generally can be used in any of the ways that antibody 1-7F9 is described as being used in WO2006003179.

The sequence of the mutated heavy chain encoding the 1-7F9(S241P) variant is shown in FIG. 1. The mutant was expressed in CHO cells, upon transfection of the mutated heavy chain and the wild-type light chain. Of course, these methods are only exemplary in that such an antibody molecule can be generated by any suitable method (examples of which are described in WO2006003179).

Various methods for producing, identifying, and characterizing (for example, the affinity (Kd)) neutralizing and/or cross-reactive anti-KIR antibodies, as well as methods for recombinant expression of such antibodies and other relevant techniques, are known in the art and described in, e.g., WO2006003179, WO2006072626, WO2005003172, and WO2005003168, all of which are hereby incorporated by reference in their entireties.

Pharmaceutical Formulations

In one aspect, the invention provides pharmaceutically acceptable antibody formulations. Of course, while exemplified with of 1-7F9 IgG4 anti-KIR antibody or the above-described 1-7F9 variant IgG4 molecule (which may be referred to as, e.g., "1-F79v", "1-7F9 S241P", or the "S241P variant", etc.), the properties of such formulations can be applicable to formulations comprising similar IgG4 antibodies, particularly similar anti-KIR IgG4 antibodies and/or cross-reactive anti-KIR antibodies. For example, any of the human anti-KIR antibodies described in WO2006003179, as well as a humanized IgG4 variant of a murine anti-KIR antibody such as DF200, NKVSF1, EB6, or GL183, with or without an S241P mutation, can be similarly used in a formulation according to the invention.

The invention also provides such formulations or other compositions comprising variant 1-7F9 antibody. Such compositions can be characterized as having less than about 15%, such as less than about 10% (e.g., about 5% or less, about 4% or less, about 3% or less, or even about 1% or less) of IgG4 "half-antibodies" (comprising a single heavy chain/light chain pair). Such IgG4 "half-antibody" by-products form due to heterogeneity of inter-heavy chain disulphide bridges in the hinge region in a proportion of secreted human IgG4 (see Angal et al., *Molecular Immunology*, 30(1):105-108, 1993 for a description of IgG4 "half-antibodies", S241P mutation, and related principles). This effect is typically only detectable under denaturing, non-reducing conditions. In the 1-7F9 variant, the S241P mutation is capable of reducing the formation of such half-antibody products. Significant reduction in the formation of half-antibodies was observed by standard techniques.

In one aspect, the invention provides a pharmaceutically acceptable and active formulation comprising (a) about 0.05 mg/mL to about 10 mg/mL of an IgG4 antibody; (b) about 10-50 mM sodium phosphate; (c) about 160-250 mM sucrose or about 100 mM NaCl; and (d) polysorbate 80, at a pH of about 7. The antibody is typically a neutralizing anti-KIR antibody, and may also be cross-reactive. In separate embodiment, the antibody comprises a heavy chain sequence according to SEQ ID NO:3 or SEQ ID NO:1. In another embodiment, the antibody further comprises a light chain sequence according to SEQ ID NO:2. The concentration of IgG4 antibody molecules in such a formulation may, for example, be in the range of about 1 to about 10 mg/ml, such as, e.g., about 10 mg/ml. In a specific embodiment, the sodium phosphate varies from about 20 to about 50 mM, the sucrose from about 220 to about 250 mM, and the polysorbate may, for example, be about 0.001%. In another specific embodiment, the sodium phosphate concentration is about 20 mM and the sucrose concentration about 220 mM.

In another exemplary aspect, the invention provides a pharmaceutically acceptable and active formulation comprising (a) about 0.05 mg/mL to about 10 mg/mL of an IgG4 antibody molecule comprising a heavy chain comprising a variable region according to SEQ ID NO:3 and a light chain comprising a light chain variable region according to SEQ ID NO:2; (b) about 50 mM sodium phosphate; (c) about 250 mM sucrose; and (d) about 0.001% polysorbate 80, at a pH of about 7. In one embodiment, the heavy chain comprises the sequence of SEQ ID NO:1.

In yet another illustrative facet, the invention provides a pharmaceutically acceptable and active formulation comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 50 mM sodium phosphate; (c) about 250 mM sucrose or about 100 mM sodium chloride; and (d) about 0.001% polysorbate 80, wherein the formulation has a pH of about 7. In a particular aspect, the antibody is 1-F79 with an S241P mutation.

In one exemplary aspect, the invention provides a pharmaceutically acceptable and active formulation comprising (a) about 0.05 mg/mL to about 10 mg/mL of an IgG4 antibody molecule comprising a heavy chain comprising a variable region according to SEQ ID NO:3 and a light chain comprising a light chain variable region according to SEQ ID NO:2; (b) about 20 mM sodium phosphate; (c) about 220 mM sucrose; and (d) about 0.001% polysorbate 80, at a pH of about 7. In one embodiment, the heavy chain comprises the sequence of SEQ ID NO:1.

In yet another illustrative facet, the invention provides a pharmaceutically acceptable and active formulation comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 20 mM sodium phosphate; (c) about 220 mM sucrose or about 100 mM sodium chloride; and (d) about 0.001% polysorbate 80, wherein the formulation has a pH of about 7. In a particular aspect, the antibody is 1-F79 with an S241P mutation.

In another exemplary aspect, the invention provides a pharmaceutically acceptable and active formulation prepared from a mixture of ingredients comprising (a) an amount of an IgG4 antibody molecule comprising a heavy chain comprising a heavy chain variable region according to SEQ ID NO:3 and a light chain comprising a light chain variable region according to SEQ ID NO:2 such that the concentration of antibody in the formulation is about 10 mg/mL; (b) about 8.4 mg/mL sodium phosphate dibasic (heptahydrate); (c) about 2.6 mg/mL sodium phosphate monobasic; (d) about 85 mg/mL sucrose; and (e) about 0.01 mg/mL polysorbate 80, wherein the formulation has a pH of about 7. In one aspect, the antibody comprises a heavy chain according to SEQ ID NO:1. In another aspect, the antibody is 1-F79.

In an additional aspect, the invention provides a method for preparing a formulation suitable for injection to a patient from a concentrated formulation having the characteristics described above, comprising providing a concentrated formulation that is stored at a temperature of from about 5° C., diluting the concentrated formulation with a formulation comprising components (b)-(d) of the formulation to produce a diluted (injection/infusion-ready) product, and optionally storing the diluted product at a temperature of from about 5° C. for up to about 24 hours before administration.

In still another aspect, the invention provides pharmaceutically acceptable and active formulations comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 5-20 mM sodium phosphate (e.g., about 5 mM sodium phosphate, about 10 mM sodium phosphate, about 15 mM sodium phosphate, or about 20 mM sodium phosphate); (c) about 180 to about 250 mM sucrose (e.g., about 180-240 mM, such as about 190-230 mM, such as about 200-225 mM, such as about 220 mM); and (d) about 0.001 or about 0.01-0.1% polysorbate 80 (such as about 0.02-01.%, 0.03-0.1%, 0.05-0.09%, 0.05-0.08%, etc.), wherein the formulation has a pH of about 7. In one aspect, the formulation comprises less than about 35 mM (e.g., less than about 25 mM) sodium phosphate. Lower sodium phosphate concentrations can be particularly desirable where long term frozen storage of the formulation is desired. In another aspect, the formulation comprises more than about 0.005% polysorbate 80. In a particular exemplary aspect, the antibody contained in such a formulation is 1-F79. In another particular illustrative aspect, the antibody in such a formulation has a heavy chain that consists or consists essentially of SEQ ID NO:1. In still another aspect, the antibody is another IgG4 antibody, such as another anti-KIR IgG4 antibody, or such as another anti-KIR antibody cross-reacting with at least KIR2DL1 and KIR2DL2/3. In one aspect, the formulation can be characterized as being isotonic.

As a further aspect, the invention provides a method for preparing a formulation suitable for injection to a patient from a concentrated formulation having the characteristics of the formulation according to the preceding paragraph, comprising providing a concentrated formulation that is stored at a temperature of from about 5° C., diluting the concentrated formulation with either a formulation comprising components (b)-(d) of the formulation or a sterile isotonic saline solution to produce a diluted (injection/infusion-ready) product, and optionally storing the diluted product at a temperature of from about 5° C. for up to about 24 hours before administration. For example, the method may include diluting such a formulation in a diluent prepared from mixing ingredients comprising about 5 g/L sodium phosphate dibasic (dihydrate), about 3 g/L sodium phosphate monobasic (monohydrate), about 85 g of sucrose, about 0.01 g of polysorbate 80 (Tween 80), which is pH adjusted with sodium hydroxide/hydrogen chloride and set to the desired volume by addition of sterile water for injection.

In another aspect, the invention provides a formulation comprising sodium chloride as a tonicity modifier, typically in place of sucrose in the above-described formulations. Typically, the concentration of sodium chloride will be about 20 mM to about 300 mM, and more typically about 50 mM to about 200 mM, such as about 75 mM to about 175 mM (e.g., about 90-160 mM, about 100-150 mM). In one aspect, such a formulation comprises sodium chloride in a concentration of about 100 mM.

In a further alternative embodiment, the invention provides a formulation in which a Tris (base) buffer is incorporated in the formulation, typically in place of sodium phosphate. Any suitable concentration of Tris (base) can be used. A concentration of about 10-100 mM, such as about 15-80 mM, 20-75 mM, or 10-60 mM, or more particularly such as about 25 mM, is typical.

A formulation according to any of the aspects of the invention can have any suitable concentration of the antibody. Typically, the concentration is about 0.05 mg/mL to about 10 mg/mL (e.g., about 1 mg/mL to about 5 mg/mL). In one exemplary aspect, the formulation is provided as a relatively concentrated antibody formulation, which may be, e.g., a formulation that is to be diluted prior to administration (typically by intravenous administration or direct parenteral injection) having a concentration of about 10 mg/mL. In another exemplary aspect, the formulation is provided as a relatively dilute formulation, such as a formulation that is infusion/injection-ready, wherein the concentration of the antibody in the formulation is about 0.05 mg/mL or about 0.1 mg/mL. In another aspect, the formulation has an antibody concentration of about 1 mg/mL.

A unit dose container of a formulation according to the invention can be provided in any suitable volume. Typically a formulation is provided in a volume of about 1 mL to about 20 mL, such as a volume of about 3 mL to about 15 mL. Commonly, the formulation is in a volume of about 5 mL to about 10 mL (and often either in 5 mL or 10 mL). The container can be any suitable type of container. The container may have spare volume (e.g., the container may be a 6 mL vial containing 5 mL of the formulation). Not all of the volume of a unit dose container may be used in a particular therapeutic regimen. The volume typically selected to provide an amount that encompasses a typical range of dosages provided to patients without unnecessarily wasting drug product.

An acceptably low level of antibody molecule precipitation in the context of this invention means that there is detectably (and preferably substantially, if not significantly) less precipitation in the formulation than would be obtained with an otherwise substantially identical formulation comprising other common pharmaceutical excipients, such as NaCl; a poloxamer surfactant, EDTA, HSA, HP-betaCD, polysorbate 80, and/or a combination of polysorbate 80 and NaCl. Methods for assessing precipitates are known in the art and may include, e.g., visual inspection using standard techniques (exemplified herein). It has been determined that a formulation of such an IgG4 antibody and about 180-500 mM (e.g., about 180-280 mM) sucrose can provide a remarkably low level of precipitates in association with an anti-KIR antibody, such as 1-F79 or 1-F79v, as compared to other typical excipients, particularly at a pH of about 7 or of about 7.0 (as compared to a pH of 6.0 or less and, to a lesser extent, a pH of 7.4). Moreover, sucrose can provide advantageous tonicity to such a formulation.

An acceptable level of antibody molecule stability (in terms of maintenance of monomeric structure and secondary structural elements) in the context of this invention means that the pH of the composition is maintained close enough to 7 to maintain monomeric structure and secondary structural elements of the antibody molecule, as compared to the stability of the molecule at a pH of, e.g., 3 or 8.5.

An acceptably low level of aggregation/precipitate formation means that the formulation contains a level of aggregation/precipitation obtained by the indicated amounts/concentrations of polysorbate 80 and sodium phosphate (in addition to sucrose). It has been determined that such formulations are associated with excellent stability and low levels of aggregation, as may be determined by, e.g., IEF, GP HPLC, and SDS PAGE analysis of the composition, for extended periods (e.g., up to about 1 month, about 2 months, about 3 months, or longer) at various temperatures (e.g., about −20° C. to about 40° C., such as about 5° C. (e.g., 2-8° C.) to about 20° C.), while also exhibiting less precipitate than histidine and tris formulations.

As noted above, a formulation according to any of the aspects of the invention desirably comprises at least one, if not two, or all three of these characteristics.

From the foregoing it can be seen that the pH of the formulation is an important factor. A limited amount of variation in a particular pH range may be acceptable (depending on the desired stability characteristics and planned storage time and variables for the formulation). In general, a pH of at least about 6 and less than about 8 (and more generally less than about 7.7, 7.6, or 7.5) is used (e.g., in a range of 6-7.4, such as 6-7.2, such as 6-7, 6.2-7, 6.4-7, 6.5-7, 6.7-7, etc.). Formulations with a pH in the range of 7-7.4, such as formulations having a pH of about 7, also have been shown to have adequate or sometimes advantageous properties.

The stability of a formulation according to any of the aspects described herein can also be characterized on the basis of the lack of high molecular weight impurities (e.g., impurities that suggest aggregation (multimers) of antibody molecules in the formulation). In one aspect, a formulation according to the invention can be characterized as having a high molecular weight (HMW) impurity content of less than about 10% (such as about 5% or less) for at least one day, such as at least about one week, such as at least about 2 weeks, at least about 1 month, at least about 2 months, or even at least about 3 months of storage at about 5° C.

Further, the formulations according to any of the aspects described herein can advantageously be applied in any of the dosage regimens provided herein in a method of potentiating NK cell activity in a patient in need thereof.

A formulation according to any of the aspects of this invention can be injected or infused at any suitable volume. Typically (e.g., for a 50-100 kg patient) a solution of about 0.3-30 mL of a diluted (either with, e.g., isotonic sterile saline solution or "placebo" formulation/diluent (i.e., formulation lacking any of the antibody or other active agents)) or undiluted final formulation is injected, usually through a 1 mL-30 mL syringe (e.g., using a syringe pump), over a period of about 1 hour, in an administration protocol. The volume will, of course, vary with the desired dosage, as exemplified by the following exemplary dosage regimen chart, where, in a specific embodiment, the anti-KIR antibody is Anti-KIR(1-7F9) with or without S241P mutation:

TABLE 2

Exemplary Dosage Volumes

| Dose Level | Dose (mg/kg) | Concentrations of anti-KIR antibody (mg/ml) | Dosing solutions (DS) or undiluted anti-KIR antibody (10 mg/ml) | Injection volume for 50-100 kg patient | Amount anti-KIR antibody vials or DSneeded per patient | Syringe size to be used (SP = Syringe Pump) |
|---|---|---|---|---|---|---|
| 1 | 0.0003 | 0.05 | Dosing Solution 0.05 mg/ml | 0.3-0.6 ml | 1 (DS) | 1 ml |
| 2 | 0.003 | 0.1 | Dosing Solution 0.1 mg/ml | 1.5-3 ml | 1 (DS) | 2 or 3 ml |
| 3 | 0.015 | 1.0 | Dosing Solution 1.0 mg/ml | 0.75-1.5 ml | 1 (DS) | 1 or 2 ml |
| 4 | 0.075 | 1.0 | Dosing Solution 1.0 mg/ml | 3.75-7.5 ml | 1 (DS) | 5-10 ml (SP) |
| 5 | 0.3 | 10 | Undiluted | 1.5-3.0 ml | 1 | 5 ml (SP) |
| 6 | 1.0 | 10 | Undiluted | 5.0-10 ml | 1 | 5-10 ml (SP) |
| 7 | 3.0 | 10 | Undiluted | 15-30 ml | 2-3 | 30 ml (SP) |

Doses and Dosage Regimens

In one aspect, the invention provides a method of potentiating NK cell activity in a patient in need thereof comprising administering to the patient a composition comprising an anti-KIR antibody in a dosage of about 0.0003 mg (antibody)/kg (patient weight) to about 3 mg/kg (e.g., about 0.003 mg/kg to about 3 mg/kg, such as about 0.015 to about 3 mg/kg, e.g., any of about 0.075 mg to about 3 mg/kg, about 0.3 mg/kg to about 3 mg/kg, and about 1 mg/kg to about 3 mg/kg, or any of about 0.0003 mg/kg, about 0.003 mg/kg, about 0.015 mg/kg, about 0.075 mg/kg, about 0.3 mg/kg, about 1 mg/kg, and about 3 mg/kg). In one embodiment, the composition is an antibody formulation described in any of the preceding sections. In one embodiment, the method comprises repeating the administration at least once, for example with a dosing frequency in the range of 3 times per day to once per 2 months. The dose may also be administered, e.g., at least 3 times, at least 6 times, or at least 10 times. In one embodiment, the antibody is administered intravenously. In another embodiment, binding of the antibody to an inhibitory KIR on the surface of an NK cell potentiates the cytotoxic activity of the NK cell. In yet another embodiment, the antibody is a cross-reactive anti-KIR antibody. For example, the antibody may comprise the variable heavy (SEQ ID NO:3) and variable light (SEQ ID NO:2) region sequences of antibody 1-7F9. Additionally or alternatively, the antibody may comprise a heavy chain comprising the sequence of SEQ ID NO:1. Typically, though not necessarily, the patient has increased CD107a levels on NK cells in blood at about 24 hrs after the first dose.

The dosage range was obtained by pharmacokinetic and pharmacodynamic (PK/PD) modelling, using cross-reactive and neutralizing anti-KIR antibody 1-7F9 as an example, as described herein. Human PK was predicted by assessing typical PK for human IgG molecules, the estimated PK obtained from monkey studies of 1-7F9, and allometric scaling between mouse and monkey. The dose also was selected to provide a detectable saturation (>20%), though not necessarily saturation (95%<) in human patients (0.0003 mg/kg, given i.v., is, for example, predicted to result in a transient saturation of up to 50% of the maximum and to be associated with a maximum plasma concentration ($C_{max}$) of about 0.006 μg/mL. These parameters (e.g., having receptor saturation of at least about 20%, such as at least about 40%, at least about 50%, at least about 90%, or at least about 95%, and/or a $C_{max}$ of about 0.005-0.01 μg/mL) also or alternatively can be used as defining characteristics for dosage regimens. The method typically includes assessing the patient for such NK cell potentiation and/or anti-tumor activity (which may be performed by use of any suitable technique, several of which being known in the art, including, e.g., KIR occupancy level, CD107a marker, etc., as described herein). The formulation is typically administered by i.v. administration over a suitable period of time, such as about 1 hour.

In another aspect, the invention provides a method of treating a disease, condition, or disorder associated with inhibition by KIR2DL1, -2 and -3 and/or 2DS1 and -2 in a patient (subject) comprising administering to the patient a composition comprising an anti-KIR antibody according to any of the dose-dosage regimens described in Table 1 so as to treat the disease, condition, or disorder. In one embodiment, the composition is any one of the above-described compositions or formulations. The term "treatment" herein refers to the delivery of an effective amount of such a formulation with the purpose of preventing any symptoms or disease state to develop or with the purpose of easing, ameliorating, or eradicating (curing) such symptoms or disease states already developed. The term "treatment" is thus meant to include prophylactic treatment. However, it will be understood that therapeutic regimens and prophylactic regimens of the invention also can be considered separate and independent aspects of this invention. As such, wherever the term is used herein it is to be understood as also providing support for such separate prophylactic and palliative/curative applications.

For example, the invention provides a method of treating cancer or a viral disease in a patient, comprising administering an anti-KIR antibody at a dose and a dosing frequency achieving at least about 90%, preferably at least about 95% KIR occupancy on NK cells in plasma for at least about three months. In separate embodiments, the dose is in the range from about 0.0003 to about 3 mg/kg; from about 0.003 to about 3 mg/kg; from about 0.015 to about 3 mg/kg; from about 0.075 to about 3 mg/kg; from about 0.075 to about 3 mg/kg; from about 0.3 to about 3 mg/kg, and from about 1 to about 3 mg/kg. Exemplary doses are about 0.0003, about 0.003, about 0.015, about 0.075, about 0.3, about 1, and about 3 mg/kg. The dosing frequency may be in the range of once per day to once per 2 months, from about once per week to about once per 2 months; or about once per month. Alternatively, the dosing frequency can be selected from about three times, about twice, and about once per day; about five times, about four times, about three times, and about twice per week; and about once every two, four, and six weeks. In other separate embodiments, a dose of from about 0.075 to about 0.3 mg/kg is administered from about 2 times per week to about once per month; a dose of from about 0.3 to about 1 mg/kg is administered from about once to about twice per month; a dose of from about 1 to about 3 mg/kg is administered from about once per month to about once per 2 months. Also, the dose and dosing frequency can be selected for those in Table 1. The dose can be, e.g., administered at least 3 times, at least 6 times, or more. For example, the method may comprise administering an anti-KIR antibody at a dose and a dosing frequency achieving at least about 95% KIR occupancy on NK cells for at least about six months. The antibody is typically administered intravenously, but other suitable administration modes are known, and also described in, e.g., WO2006003179. The antibody is preferably a neutralizing and/or a cross-reactive anti-KIR antibody, such as, e.g., Anti-KIR(1-7F9) or its S241P variant.

In one aspect, the patient to be treated by the above-described method is a patient diagnosed with cancer. In a more particular aspect, the patient is a patient diagnosed with acute myeloid leukaemia (AML). In another particular aspect, the patient is a patient diagnosed with chronic myeloid leukaemia (CML). In still another particular aspect, the patient is a patient diagnosed with multiple myeloma (MMy). In yet another exemplary aspect, the patient is a patient diagnosed with non-Hodgkin's lymphoma (NHL). In another illustrative aspect, the patient to be treated by the practice of the above-described method is a patient diagnosed with colorectal cancer. In yet another aspect, the patient to be treated by the practice of the method is a patient diagnosed with renal cancer. In still another facet, the patient is a patient diagnosed with ovarian cancer. In another embodiment, the patient is a patient diagnosed with lung cancer. In yet another embodiment, the patient is a patient diagnosed with breast cancer. In a further embodiment, the patient is a patient diagnosed with malignant melanoma. In still another particular embodiment, the patient to be treated by the above-described method is a patient diagnosed with an infectious disease, such as a viral infection (e.g., an infection with HIV or Hepatitis C).

The effect of the therapy on the patient may be followed by assessing the levels of NK cell activation markers or tumor markers in a biological sample taken from the patient, such as blood, plasma, urine, or the like. For example, as shown in the Examples, most patients has increased CD107a levels on NK cells in a blood sample taken 24 hrs after the first dose of 1-7F9, even though very low doses were administered. Notably, this increase of CD107a could not be detected on T cells. Particular tumor markers selected for the clinical studies described herein and useful to monitor treatment include, e.g., Wilms' tumor gene 1 transcript in blood and/or bone marrow in AML patients, and the levels of M-protein in urine. Further, based on the role of NK-cells in anti-tumor activity towards various other cancers, a decrease in the level of other tumor markers, including CEA in colorectal cancer, AFP and HCG in germ cell tumors, HCG in trophoblastic tumor, CA-125 in ovarian cancer, CA 15-3, CA 27.29, and oestrogen receptors in breast cancer, PSA in prostate cancer, CD5+/CD23+ cells in chronic lymphocytic leukemia, as well as cytogenetic markers in leukemia's and lymphomas is expected in malignancies susceptible to anti-KIR treatment. Additionally or alternatively, the efficacy of anti-KIR therapy of malignant diseases can be assessed by standard end-points like cancer-free survival, overall survival, and/or event-free survival (see, e.g., Brune et al. (Blood. 2006; 108:88-96), for description of a Phase III trial in AML patients).

While Anti-KIR(1-7F9) or its S241P variant is a preferred antibody for modulating NK cell activity and/or treatment of cancer, viral diseases, or other suitable diseases, other anti-KIR antibodies may also be used in the methods and dose-dosage regimens according to the invention. Such anti-KIR antibodies should, however, have similar Kd values, similar clearance in a patient, and a similar volume of distribution, as Anti-KIR(1-7F9), where "similar" means within about 50%, preferably within about 30% of the corresponding Anti-KIR(1-7F9) parameter. Anti-KIR(1-7F9) has a high affinity Kd of about 4 ng/ml, and low affinity Kd of about 20 ng/ml for doses up to 0.015 mg/kg; a clearance of about 0.5 ml/h/kg, and a volume of distribution of about 115 ml/kg (see Example 11). An exemplary anti-KIR antibody useful in one or more methods of the invention has the following properties: (a) reduces or blocks the signalling of an inhibitory KIR on NK cells; (b) a high affinity Kd from about 2 to about 6 ng/ml; (c) a low affinity Kd from about 10 to about 30 ng/ml; (d) a clearance of from about 0.25 to about 0.75 ml/h/kg, (e) a volume of distribution of from about 50 ml/kg to about 175 ml/kg, and (f) optionally binds more than one KIR, e.g., at least all of KIR2DL1, KIR2DL2, and KIR2DL3.

In another aspect, any of the above-described methods can be further complemented by administering a secondary anti-cancer agent, such as those described in WO2006003179 (an immunomodulatory agent, a hormonal agent, a chemotherapeutic agent, an anti-angiogenic agent, an apoptotic agent, a second antibody that binds to an inhibitory KIR, an anti-infective agent, a targeting agent, and an adjunct compound, such as, e.g., an anti-CD20 antibody). The variant antibody of the invention also may be provided in an article of manufacture or "kit" with an effective dosage of such a secondary agent. The invention further provides an isolated nucleic acid encoding the variant antibody, a method of producing the antibody by the expression of such a nucleic acid in an appropriate host cell (and recovering the antibody product therefrom by any suitable method), a host cell comprising such a nucleic acid, and a vector comprising such a nucleic acid.

EXAMPLES

The following exemplary experimental methods and data are presented to better illustrate various aspects of the invention, but in no event should be viewed as limiting the scope of the invention.

Example 1—1-F79 Stability Studies

The biophysical properties and stability of human antibody 1-7F9 were studied as follows. The folding and secondary structure of the protein was studied by circular dichroism (CD) and the oligomerization and aggregation by dynamic light scattering (DLS). In order to mimic storage conditions for two years at 5° C. the protein was subjected to incubation at 37° C. with shaking for 14 days.

Materials and Methods
Sample Preparation.
2 mg/ml 1-7F9 was prepared in (a) 50 mM Na-Phosphate, 0.001% Polysorbate 80 (Sigma, P8074), pH 7.0; (b) 50 mM Na-Phosphate, 0.001% Polysorbate 80, pH 7.0, 0.5 mM Sucrose; (c) 50 mM Citrate, 0.001% Polysorbate 80, pH 3.0; and d) 50 mM Tris, 0.001% Polysorbate 80, pH 8.5.

Circular Dichroism (CD).
CD measurements were performed at 25° C. with a protein concentration of 2.0 mg/ml on a Chirascan circular dichroism spectrometer (Applied Photophysics) equipped with a peltier element for temperature control. 1-7F9 samples were in cylindrical quartz cells with 0.1 mm path length. Buffer scans were recorded and subtracted for each sample spectra.

Dynamic Light Scattering (DLS).
DLS was performed at 25° C. with a protein concentration of 2.0 mg/ml using a Dynapro 99 temperature controlled DLS instrument (Protein Solutions Inc.). Data analysis was performed using the Dynamics software supplied with the instrument.

Results
Whereas the molecular size did not change for the samples at pH 7.0 after 14 days incubation as evaluated by DLS, both the samples formulated at pH 3.0 and pH 8.5 aggregated heavily during a 14 day period.

The CD measurements showed characteristics of an all beta structure and revealed that the samples formulated at pH 7.0 maintained their secondary structure throughout the accelerated study, although there was a slight drop in the signal for the sample containing only Polysorbate 80 as excipient. This might be due to a weak precipitation of the sample since the overall form of the spectra is unchanged. The sample containing sucrose showed no such decrease over time. The CD measurements of the samples formulated at pH 3.0 and 8.5 showed a strong change in spectral characteristics over time, probably as a result of unfolding or other conformational changes, which could lead to non-functional 1-7F9 protein. The changes were observed immediately and were most significant at pH 3.0.

Overall, 1-7F9 maintained its physical properties and remained stable under stressed conditions (37° C. with shaking) at pH 7.0 with Polysorbate 80 and Sucrose as excipients.

Example 2—Solubility Screening

Figure 3:
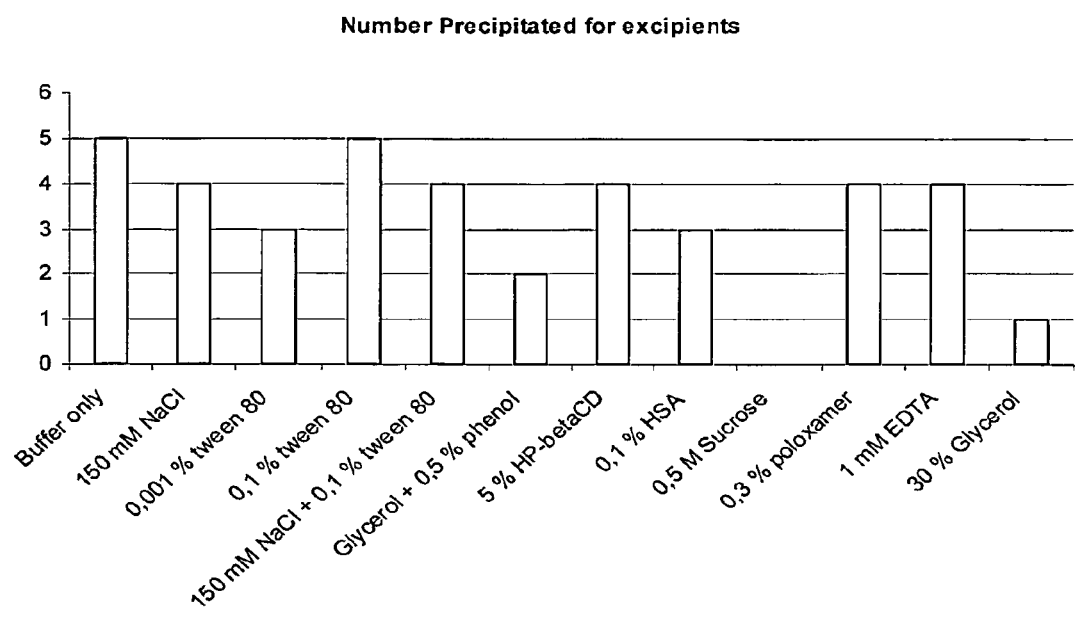
FIG. 3 shows the results of a precipitation analysis associated with different excipients.

A microformulation screen which tests 88 different conditions in 1 μl drops was performed on formulations containing anti-KIR human IgG4 antibody 1-F79. The conditions in the screen involved a pH range between 3-10 and the addition of several known excipients. All formulations where inspected visually for precipitation (assessing product clarity, color, and the presence of particles/fibers). For visual assessments, appearance was assessed independently by two operators against daylight (typically) or general laboratory lighting against black and white backgrounds. The results from the pH solubility study are presented in FIG. 2 and the results of the precipitation analysis associated with the different excipients are shown in FIG. 3.

The results of this analysis show that less precipitation occurred at pH 7.0 as compared to pH 6.0 and 7.4, and that even less precipitation occurred at pH 5.0, 3.0, and 8.5. From the data presented in FIG. 2, it can be seen that a 0.5 M sucrose formulation resulted in no detectable precipitates (glycerol formulations also were associated with a relatively low level of precipitates).

Example 3—Formulation Study

Twelve different formulations of 1-F79 (10 mg/mL) were analyzed based on pH, appearance, GP HPLC, SDS-PAGE, and IEF, over a storage period of up to three months at four different temperatures, according to the schedule in Table 3. The formulations tested are shown in Table 4.

TABLE 3

Testing Protocol for Stability Assessments

| Temperature | Time point (months) | | | |
|---|---|---|---|---|
| | 0 | 1 | 2 | 3 |
| −20° C. | X | X | NT | NT |
| 5° C. | X | X | X | X |
| 25° C. | X | NT | X | X |
| 40° C. | X | X | X | NT |

X = tests performed;
NT = not tested

TABLE 4

Tested formulations

| Code | Formulation | pH |
|---|---|---|
| F1 | 25 Mm sodium acetate, 125 mM sodium chloride, 0.001% Tween 80 | 5.5 |
| F2 | 25 Mm sodium acetate | 5.5 |
| F3 | 40 mM sodium citrate, 125 mM sodium chloride, 0.001% Tween 80 | 5.5 |
| F4 | 40 Mm sodium citrate | 5.5 |
| F5 | 50 mM sodium phosphate, 100 mM sodium chloride, 0.001% Tween 80 | 7.0 |
| F6 | 50 mM sodium phosphate | 7.0 |
| F7 | 50 mM sodium phosphate, 250 mM sucrose, 0.01% Tween 80 | 7.0 |
| F8 | 50 mM sodium phosphate, 250 mM sucrose, 0.001% Tween 80 | 7.0 |
| F9 | 25 mM Tris (base), 125 mM sodium chloride, 0.001% Tween 80 | 7.5 |
| F10 | 25 mM sodium citrate, 150 mM sodium chloride, 0.001% Tween 80 | 5.5 |
| F11 | 25 mM L-histidine, 150 mM sodium chloride, 0.001% Tween 80 | 6.5 |
| F12 | 25 mM L-histidine, 150 sodium chloride, 0.001% Tween 80 | 6.5 |

The specific methods employed briefly were as follows (appearance testing is described above).

Gel permeation (GP) HPLC was carried out on an Agilent 1100 HPLC system using a standardized TSK SWXL G3000 column. The mobile phase was 0.2 M sodium phosphate at pH 7.0 at a flow rate of 1.0 mL/min. The sample injection volume was 50 μL. Protein loadings of 250 μg were analyzed using single determinations (% monomer, % fragment, and % fragment was determined for each sample). All samples were determined initially to have aggregate levels of between 1.8% and 2.3%.

SDS PAGE was performed to test homogeneity and purity of the product. SDS PAGE of reduced and non-reduced samples was performed using Novex pre-cast 4% and 20% (w/v) acrylamide gradient gels and electrophoresed at 125 V limiting conditions per gel until the dye front had migrated to within 1 cm of the bottom of the gel. Protein loadings of 4 μg for non-reducing conditions and 10 μg for reducing conditions were used. Gels were stained at room temperature using Coomassie Brillian Blue R250 strain. Novex MK12 molecular weight markers were included on each gel to cover a MW range of 6 kDa to 200 kDa. For reducing conditions, incubation was with sample buffer at pH 8.0 containing 2-mercaptoethanol. For non-reducing conditions, incubation was with sample buffer at pH 7.1 without 2-mercaptoethanol. Reduced and non-reduced samples were prepared separately and analyzed on separate gels to prevent contamination. A single test was performed at each endpoint. The banding profile for each sample was analyzed visually for non-reduced and reduced samples and by laser densitometry for determination of the relative percentage purity for each band for reduced samples.

IEF was performed using commercially available agarose isoelectric focusing gels, pH 3 to pH 10, to determine the isoelectric focusing pattern and isoelectric point range of proteins. 10 μg of each sample was loaded in a volume of 5 μL to the cathode end of the gel. Following focusing for 1500 volt hours, the gels were stained with Coomassie Brilliant Blue R250 stain and the focused pattern for each sample compared visually with the T=0 profile to identify any change in the charged isoforms of the protein. Appropriate pI markers were included on each gel and identified based on the pH values supplied by the manufacturer. Each sample was tested singly at each time point.

The mean antibody protein concentration in the twelve formulations was 10.61 mg/mL and all samples had a protein concentration within 3% of this value.

The various formulations were scored in terms of particulates at these time points based on these tests (a score of 0 being the best and 14 being worst) and on a 3-point scale in terms of stability (0 being worst, 1 indicating a formulation with possible "lead candidate" properties, and 2 indicating a formulation with "lead candidate" quality) for the other assays performed as part of the analysis (HPLC, IEF, SDS, and appearance analysis). The results obtained from this work are provided in Tables 5 and 6:

TABLE 5

Analysis of Particle Formation in Various 1-F79 Formulations

| Formulation | Temperature (° C.) | | | |
|---|---|---|---|---|
| | −20 | 5 | 25 | 40 |
| F1 | 1 | 2 | 1 | 6 |
| F2 | 1 | 1 | 1 | 4 |
| F3 | 2 | 3 | 1 | 10 |
| F4 | 3 | 3 | 0 | 14 |
| F5 | 0 | 2 | 1 | 1 |
| F6 | 6 | 2 | 0 | 1 |
| F7 | 0 | 0 | 0 | 4 |
| F8 | 0 | 2 | 0 | 2 |
| F9 | 0 | 0 | 0 | 1 |
| F10 | 2 | 2 | 1 | 3 |
| F11 | 2 | 1 | 0 | 3 |
| F12 | 0 | 1 | 1 | 3 |

TABLE 6

Stability Analysis of 1-F79 Formulations

| SAMPLE | GP HPLC | SDS | APPEARANCE | IEF | Total Score |
|---|---|---|---|---|---|
| F1 | 0 | 0 | 0 | 0 | 0 |
| F2 | 2 | 1 | 2 | 0 | 5 |
| F3 | 0 | 0 | 0 | 0 | 0 |
| F4 | 0 | 0 | 2 | 0 | 2 |
| F5 | 2 | 1 | 2 | 1 | 6 |
| F6 | 1 | 1 | 2 | 1 | 5 |
| F7 | 0 | 1 | 2 | 1 | 4 |
| F8 | 0 | 1 | 2 | 1 | 4 |
| F9 | 2 | 1 | 2 | 1 | 6 |
| F10 | 0 | 0 | 2 | 0 | 2 |
| F11 | 2 | 2 | 0 | 2 | 6 |
| F12 | 2 | 2 | 0 | 2 | 6 |

Specific particular results include the following. GP HPLC data indicated that at about 25° C. and about 40° C., there was a marked decrease in monomer levels (indicating, e.g., aggregation/multimerization) and/or increase in fragment levels (indicating, e.g., proteolysis) for formulations containing acetate and citrate buffers at pH 5.5 compared with other formulations in the study over time. SDS PAGE results also indicated that at least most of the citrate and acetate formulations may be unsuitable for long term storage of an IgG4 anti-KIR antibody, particularly at higher temperatures, due to, i.a., higher levels of fragmentation compared to the other formulations. Lower pH formulations also were generally associated with greater levels of fragmentation (proteolysis).

The ability of the formulations to be subjected to freeze-thaw conditions also was assessed as part of this and other experiments. In general, the formulations exhibited suitable freeze-thaw properties, but storage at sub-zero conditions for at least some of the formulations was considered less than optimal. Formulation F6 was deemed to be unsuitable for long-term storage at sub-zero temperatures due to freeze-thaw stress. Inclusion of an appropriate tonicity modifier, such as sucrose and/or sodium chloride, can be important to storage at sub-zero conditions and/or for freeze-thaw of an antibody formulation. In general, provision, storage, and handling of the formulation as a liquid at about 5° C. is recommended. If freezing is required, relatively low amounts of sodium phosphate (if incorporated) should be used and tonicity modifier concentration/selection adjusted appropriately.

Overall, the results obtained from this analysis suggest that histidine, tris, and phosphate-based formulations containing polysorbate 80 (Tween 80) exhibit the best properties over various temperature conditions. As shown in Table 4, the formulations deemed best by IEF, HPLC, and SDS PAGE analysis contained histidine, sodium chloride, and polysorbate 80. However, these specific formulations contained precipitate and were considered to be unsuitable in terms of particle formation (particularly at higher temperatures). From the remaining data, it was determined that a phosphate formulation at pH 7, containing polysorbate 80 (Tween 80) and either sodium chloride or sucrose as a tonicity modifier would provide an optimal anti-KIR IgG4 formulation.

Example 4—Surface Plasmon Resonance Study of the Binding of Wild-Type Anti-KIR1 7F9 and anti-KIR1 7F9 S241P to Recombinant KIR2DL3

1-7F9 S241P variant was generated by applying site-directed mutagenesis, using a Quick-Change Mutagenesis kit (Stratagene), and the primers P1: 5'-cccccatgcccaccatgccagcacctgag (SEQ ID NO:4), and P2: 5'-ctcaggtgctgggcatggtgggcatggggg (SEQ ID NO:5). The mutation was confirmed by sequencing.

Surface plasmon resonance studies were performed on a Biacore 3000 instrument (Biacore AB, Uppsala, Sweden) in order to verify and compare binding of "wild-type" anti-KIR1 7F9 and anti-KIR1 7F9 S241P to immobilized KIR2DL3.

Immobilization of recombinant KIR2DL3 was conducted on a CM5 sensor chip (Biacore AB), using standard amine coupling as described by the manufacture (Biacore AB).

HBS-EP buffer (10 mM HEPES, 150 mM NaCl, 3 mM EDTA, 0.005% Polysorbat 20 (v/v)) was used as running buffer, and for all dilutions. Regeneration of the sensor chip was performed by a short pulse (15 ul, Flow 30 ul/min) of 10 mM glycin-HCl pH 1.8.

The experiment was performed at flow rate 10 ul/min. at 25° C. Data was analyzed using Biaevaluation 4.1 software.

Six different batches of CHO-cell expressed anti-KIR1 7F9 S241P, and one hybridoma expressed wild-type anti-KIR1 7F9 batch were tested. All samples were diluted to 100 nM in HBS-EP. The individual samples were passed over the immobilized KIR2DL3 for 3 min., followed by a 10 min. dissociation phase.

All samples demonstrated binding to immobilized KIR2DL3. The off-rates of the individual samples were determined using a Langmuir 1:1 binding model. All samples demonstrated nearly identical off-rates (Table 7).

TABLE 7

| Off-Rates for 1-7F9 S241P | |
|---|---|
| Sample | Off-rate |
| Anti-kir1 7F9 S241P CHO#1 | 2.07E−05 |
| Anti-kir1 7F9 S241P CHO#2 | 2.24E−05 |
| Anti-kir1 7F9 S241P CHO#3 | 3.23E−05 |
| Anti-kir1 7F9 S241P CHO#4 | 2.87E−05 |
| Anti-kir1 7F9 S241P CHO#5 | 2.72E−05 |
| Anti-kir1 7F9 S241P CHO#6 | 2.32E−05 |
| KIR1 7F9 wild-type Hybridoma | 2.83E−05 |

Based on the identical binding pattern and off-rates, these data indicate no differences between wild-type anti-KIR1 7F9 and anti-KIR1 7F9 S241P with regard to binding to KIR2DL3.

Example 5—Reduced Half-Antibody Formation in S241P 1-F79

To assess whether half-antibody formation is reduced by introduction of the S241P mutation in the heavy chain sequence of 1-F79, the following experiment was performed.

Recombinantly expressed S241 1-F79 IgG4 variant was purified on MabSelect™ SuRe protein-A columns. After loading, media columns were washed with 10 column volumes of PBS buffer and eluted with 100 mM Glycine, 100 mM NaCl buffer pH 3.0 followed by buffer exchange in to PBS buffer using a HighTrap™ Desalting column. All operations were controlled by a Äktaxpress system from GE Healthcare Amersham Biosciences AB.

Estimation of antibody heterogeneity and content of half antibodies were analyzed by the Agilent 2100 bioanalyzer using methods described in Forrer, *Analytical. Biochemistry* 334.1 (2004): 81 and Vasilyeva, *Electrophoresis* 25.21-22 (2004): 3890. Samples were prepared under non-reducing conditions with addition N-ethylmaleimide to stabilize disulphide bonds.

Figure 4:
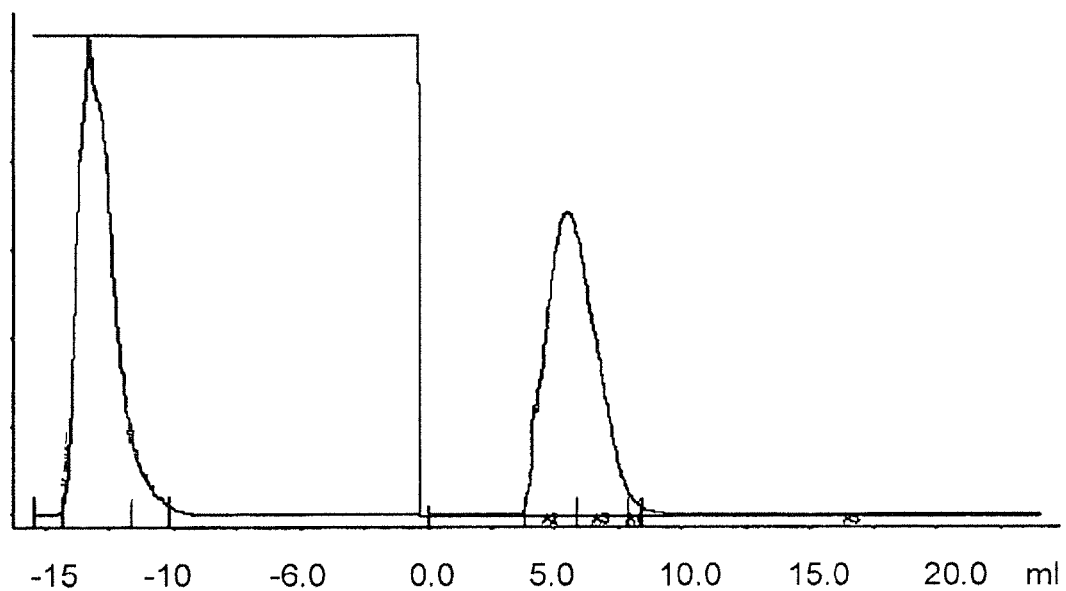
FIG. 4 shows a chromatogram from purification of Anti-KIR(1-7F9) S241P mutant using Protein A and desalting into PDS buffer. Eluted material from protein A, annotated as peak start (Retention ("R.") vol—14 mL) and peak end (R. vol—12 mL), was stored in a loop prior to injection at the desalting column. After desalting, fractions were collected and fractions annotated A2 and A3 were pooled and used for further analysis.

The expressed AntiKir1-7F9 S241P mutant, was purified using Protein A and desalteted into PBS Buffer (FIG. 4). In FIG. 4, eluted material from protein A is annotated as peak start (Retention ("R.") vol—14 mL) and peak end (R. vol—12 mL) and stored in a loop prior to injection at the desalting column. After desalting, fractions were collected and fractions annotated A2 and A3 were pooled and used for further analysis.

Figure 5A:
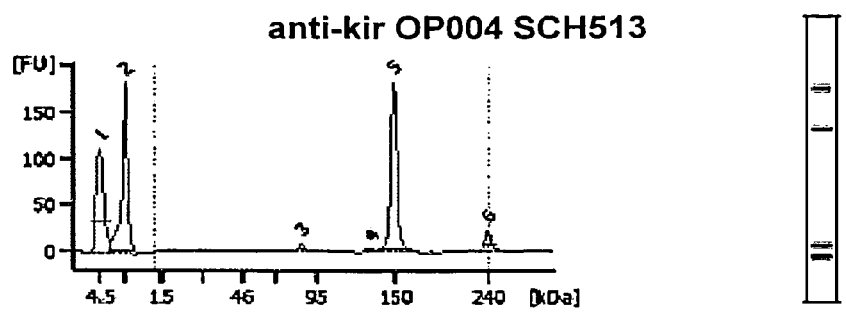
FIGS. 5A-B present electropherograms and integration tables from analyses of Anti-KIR(1-7F9) expressed in hybridoma cells (A) and Anti-KIR(1-7F9) expressed in CHO K1 cells (B).
Figure 5B:
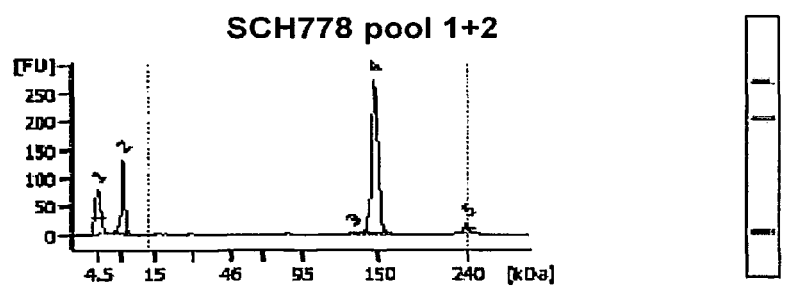

Following purification, the amounts of half antibodies present in the composition was analysed using the method previously described by Forrer and Vasilyeva, supra. Analysis of half-antibodies demonstrates that half antibody formation is suppressed by the S241P mutation (see FIG. 5 and Table 8 (below). FIG. 5 presents electropherograms and integration tables from analyses of Anti-KIR(1-7F9) expressed in hybridoma cells (left hand) panel and Anti-KIR(1-7F9) expressed in CHO K1 cells right hand panel.

Table 8 reflects the amounts of half-antibody formation detected for both wild-type (WT) 1-F79 and S241P Anti-KIR(1-F79) expressed in CHO K1 cells:

TABLE 7

Comparison of Half-Antibody Formation in 1-7F9 and 1-7F9 S241P Abs

| WT  | S241P |
|-----|-------|
| 8.6 | 0.3   |
| 9.5 | 0.6   |
| 5.8 | 0.4   |

These results demonstrate that the proline substitution of Ser-241 in the Anti-KIR(1-7F9) heavy chain results in an anti-KIR IgG4 antibody product associated with significantly less "half antibody" by-products.

Example 6—Prediction of Human PK/PD of Anti-KIR(1-7F9) Based on In Vivo Studies in KIR-Transgenic Mice This Example describes a pharmacokinetic (PK)/pharmacodynamic (PD)-based rationale for selection of the starting dose of Anti-KIR(1-7F9) in a human dose trial, predicting a dose which would result in detectable saturation (>20%), but not full saturation (<95%) of KIR-receptors in humans at the time of maximal saturation.

Specifically, a PK-model was developed to capture the PK-properties of Anti-KIR(1-7F9) in wild-type and KIR-transgenic mice. Based on the PK-model, a PK/PD model was established for the relationship between KIR-occupancy and plasma concentration in KIR-transgenic mice. The PK-profile of Anti-KIR(1-7F9) in humans was then predicted and simulated, and a PK/PD-model for occupancy of KIR in humans devised by combining the mouse PK/PD model with the predicted human PK-profile.

Materials and Methods

Data Sources.

The PK/PD model in KIR-transgenic mice was based on data from a study where the relationship between saturation of KIR-receptors and plasma concentration in vivo was determined for a range of dose levels of Anti-KIR(1-7F9) administered i.v. as a single dose. A dose range of 0.0004 mg/kg to 4 mg/kg was used. Three different strains of mice were used. The wild-type B6 (C57BL/6) mouse does not express the KIR-receptor and was used as reference for assessing the magnitude of possible target-mediated clearance in two KIR-transgenic mouse strains. A mouse strain expressing the human KIR2DL2 receptor on a subset of NK cells and T cells, similar to the pattern seen in humans, was designated KIR-transgenic II (KIR-tgII). In this model, the expression level of KIR is slightly lower than KIR on normal human NK cells. As a worst-case model in terms of total number of KIR-receptors available for target-mediated clearance, a mouse strain designated KIR-transgenic I (KIR-tgI) was chosen. The KIR-tgI mouse severely over-expresses the KIR-receptor and is not expected to reflect the pattern seen in humans.

Following single i.v. doses of Anti-KIR(1-7F9), groups of mice (n=3) were sacrificed and the blood and spleen were collected for determination of saturation of KIR-receptors by means of fluorescence-activated cell sorting (FACS) at different time points over 7 days. For each mouse, the concentration of Anti-KIR(1-7F9) was determined at one time point before sacrifice as well as at the time for determining saturation using a validated ELISA method. Receptor occupancy was measured by FACS, using both a directly conjugated Anti-KIR(1-7F9) to detect free KIR, and an anti-IgG4 antibody to measure bound Anti-KIR(1-7F9). In this manner, it was possible to follow the disappearance of free KIR with increasing doses of injected mAb, which was paralleled by an increasing amount of bound Anti-KIR(1-7F9).

In the modelling, any receptor internalisation was disregarded and only the saturation of the receptors present on the surface of the NK-cells was taken into account. Measurement of median fluorescence intensity (MFI) of labelled NK-cells was used to assess receptor occupancy and other characteristics. The prediction of human PK-parameters was based on mouse PK data from the PK-PD study, monkey PK data from an earlier study, and human IgG PK parameters from various literature sources.

Assays.

The plasma concentration for mice and monkeys was assessed using a validated ELISA-based assay. Limit of quantification was 2.5 ng/ml in the mouse plasma assay and 0.5 ng/ml in the monkey plasma assay.

In the KIR-transgenic mice, receptor occupancy by Anti-KIR(1-7F9) was measured by FACS, using both a directly conjugated Anti-KIR(1-7F9) to detect free KIR, and an anti-IgG4 antibody to measure bound Anti-KIR(1-7F9). In this manner, it was possible to follow the disappearance of free KIR with increasing doses of injected antibody, which was paralleled by an increasing amount of bound Anti-KIR (1-7F9).

For calculation of % saturation of the KIR-receptors, the total median fluorescence intensity (MFI) from the two measurements was used as described below.

Software.

The following software was used for final data file generation:

S-plus, version 6.1, Insightful Corporation, Seattle, Wash., USA.

The following software was used for nonlinear mixed-effects modelling:

Compaq Visual Fortran, version 6.6a, Hewlett-Packard Company, Palo Alto, Calif., USA.

NONMEM V, version 1.1, GloboMax, Hanover, Md., USA.

Visual-NM, version 5, RDPP, Montpellier, France.

Installation/validation of the software was carried out in the following way:

NONMEM functionality was verified using current departmental procedures.

Other software was installed as recommended by the manufacturers.

Data Files

Format Generation Procedures.

The PK and PD data were initially prepared as Excel files. Subsequently, the PK and PD data were combined and prepared for use by NONMEM and NM-TRAN using S-PLUS.

The final data file was used for the generation of the PK-model. The output from the PK-model with individual PK-estimates was used for the PD-model after excluding the irrelevant B6-mice data and adding simulation records for the purpose of simulating population means for each dose level in humans.

Handling of Missing Values and Values Below LOQ.

In the KIR-tgII mice, the FACS analysis for two mice in the 3 µg group failed and the data did not appear in the data file. PK-data: BLQ-values were set to 0 and excluded from the model building, but the time point was kept in the data file for prediction of the plasma concentration using the PK-model.

Handling of Occasional Outliers.

The plasma concentration in the 0.1 μg group in the KIR-tgII mice was considered an occasional outlier and was excluded during parameter estimation of the PK model. The group was included in the PK-PD model with predicted plasma concentrations.

Subsequent to model development, four outliers were identified and removed based on the criterion that the numerical value of the weighted residual should be less than 4.

Checking Procedures.

For the mouse PK/PD model, the final data file used for NONMEM was checked against the raw data Excel file with respect to % bound and body weight for all individuals as well as plasma concentrations for 3 individuals. For the monkey PK-model, the number of records in the data file was checked against the number of records in the raw data.

Model Development

NONMEM's first order conditional (FOCE) estimation method with or without INTERACTION as indicated in the individual models, was used for model development. Evaluation of and discrimination between intermediate models were based on objective function values and standard graphical evaluation methods.

In terms of objective function value, changes in this value were assumed to be $\chi^2$-distributed (for nested models), and criteria for expanding the model were defined and used accordingly.

Structural Models and Error Models.

For all animal PK models, exponential error models were investigated for inter-individual variability (IIV). For the PK models (using concentration as response), proportional as well as combined error models were investigated for intra-individual variability. For the PD models (using % bound as response), additive error models were used.

For the simulated human PK profiles, no intra- or inter-individual variability were taken into account.

Checking Procedures.

The final model (i.e. NONMEM control stream) was thoroughly proof-read to ensure correctness.

Covariate Analysis.

For the PK-models in mice, body weight (BW) was investigated as a covariate for all PK-parameters.

Evaluation Procedures.

Evaluation of the final model was performed by means of standard graphical evaluation methods.

Results and Discussion

Three PK-models in mouse strains were developed: 1) For wild-type B6 only, 2) for B6 and KIR-tgII mice in combination, and 3) for KIR-tgI mice.

Analysis of Wild-Type B6.

Figure 6:
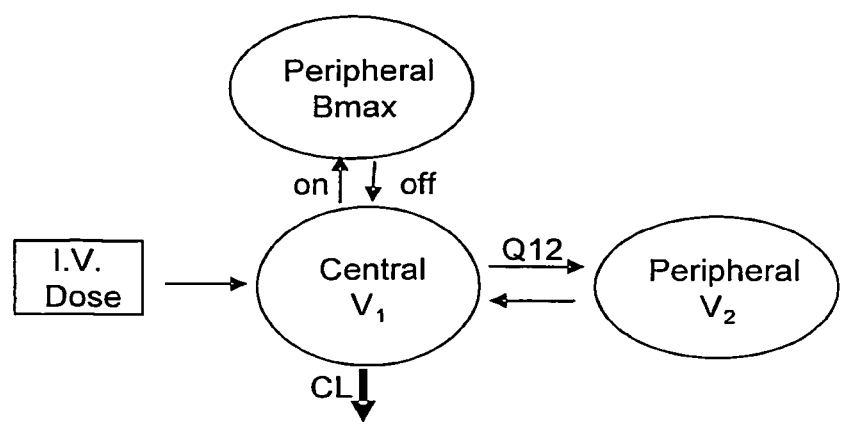
FIG. 6 shows a schematic representation of the population pharmacokinetic model for Anti-KIR(1-7F9) in wild-type B6 mice and transgenic KIR-tgII mice including a saturable peripheral binding site.

From the analysis of PK data from wild type B6, it was found that non-linearities were needed to explain the difference between the high and the low dosing groups. The chosen model used a special case of Mager & Jusko's target mediated drug disposition (TMDD) model (Mager and Jusko, J Pharmacokinet Pharmacodyn 2001; 28(6):507-532) in which only the volume of distribution is non-linear, not the clearance (see the schematic representation in FIG. 6). Alternatively, a two compartment Michaelis Menten model, i.e. with saturable clearance, could describe the PK profiles, thus making it impossible to be conclusive regarding the underlying physiological mechanism of the observed non-linearities in the PK-data. By using the TMDD model, a reasonable estimate could be obtained for clearance in the mouse model, which would not be possible with the Michaelis-Menten model, and thus, the TMDD model was adopted as the final model.

Joint Analysis of B6 and KIR-tgII Mice.

For the joint analysis of wild-type B6 and KIR-tgII mice, the TMDD model was again found to be the preferable model to explain the observed non-linearities in data. In order to investigate whether the PK could be concluded to be different in the two mouse strains, it was attempted to describe data either with identical parameters for the two strains or with different parameters in the two strains. Since visual model fits were virtually identical by these two methods, it was concluded that no difference was seen in the PK of the two strains. Note, however, that a significant difference in objective function value (OFV) was found (ΔOFV=28.4).

Figure 7:
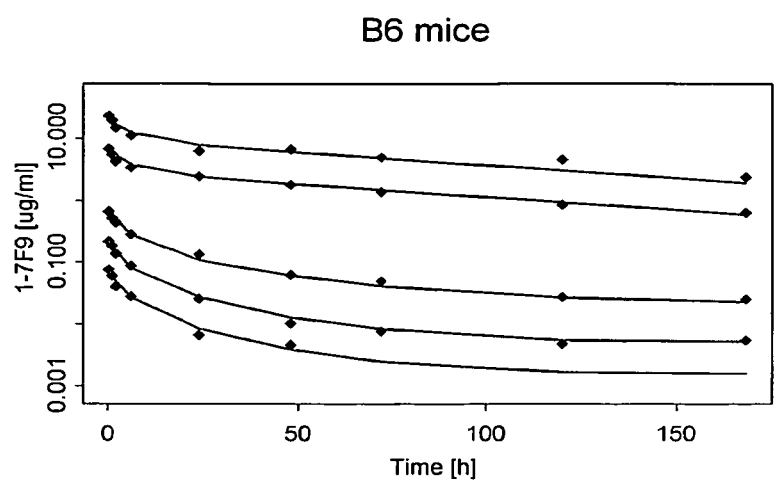
FIG. 7 shows mean predicted PK profiles compared to mean observed values in B6 mice. Model predictions are based on the combined B6/KIR-tgII PK model.
Figure 8:
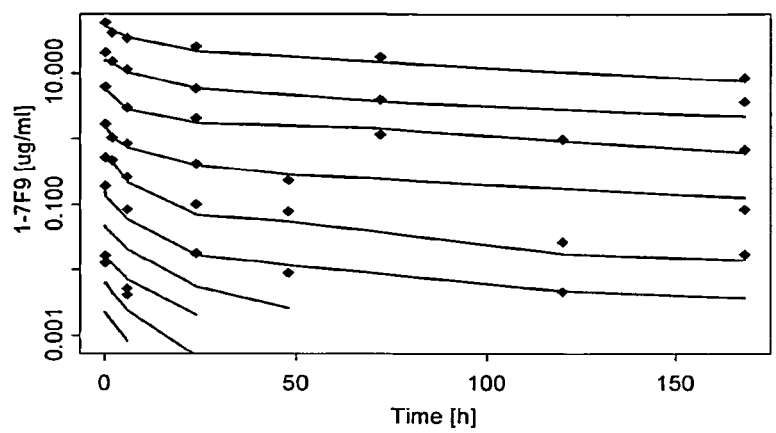
FIG. 8 shows mean predicted PK profiles compared to mean observed values for KIR-tgII mice Model predictions are based on the combined B6/KIR-tgII PK model.

Evaluation plots for the final model in B6/KIR-tgII mice showed that the quality of the model was fully acceptable, considering the amount of data available (FIGS. 7 and 8). More specifically, the agreement between observed and predicted concentrations, both on the individual level and on the population mean level, was fully acceptable. The parameter estimates for the final models are shown in Table 1 and Table 2 for B6/KIR-tgII and KIR-tgI mice, respectively.

Analysis of KIR-tgI Transgenic Mice.

Figure 9:
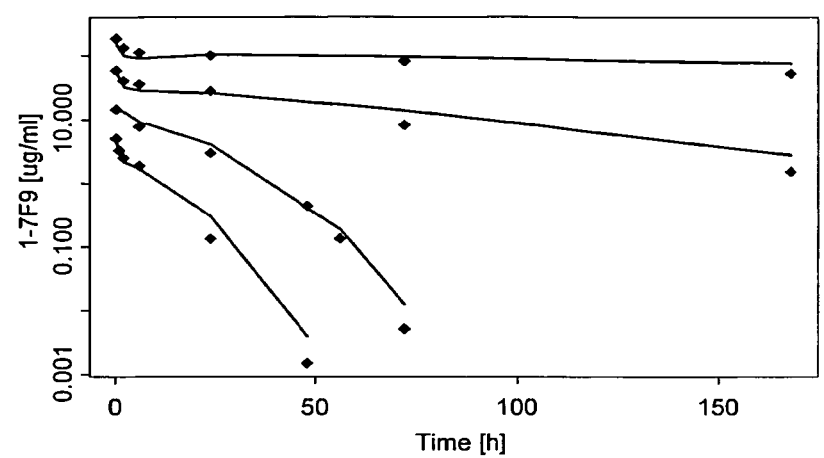
FIG. 9 shows mean predicted PK profiles compared to mean observed values in KIR-tgI mice.

The pharmacokinetics of KIR-tgI transgenic mice were found to be significantly different from the two other strains. The non-linearity was much larger, and the data were not compatible with the TMDD model, whereas a Michaelis-Menten model for saturable elimination was successful. Mean predicted PK profiles are compared to mean observed values for KIR-TGI transgenic mice in FIG. 9.

TABLE 8

Parameter estimates of the final combined PK-model for B6 and KIR-tgII mice.

| Parameter | $V_1$ (ml/g) | $V_2$ (ml/g) | $B^{max}$ (μg mAb/g) | CL (ml/h) | $Q_{12}$ (ml/h) | $K_{on}$ (l/h) | $K_{off}$ (l/h) |
|---|---|---|---|---|---|---|---|
| Population mean | 0.0689 | 0.0626 | 0.0662 | 0.0266 | 0.127 | 0.094 | 0.003 |
| % SE of mean | 2.5 | 7.7 | 19.3 | 7.3 | 12.4 | 22.2 | 8.4 |
| IIV (% of mean) | — | — | 19.5 | 37.8 | — | — | — |
| Residual SD | | | | 22.4% | | | |

TABLE 9

Parameter estimates of the final PK-model for KIR-tgI mice.

| | $V_1$ (ml/g) | $V_2$ (ml/g) | $Q_{12}$ (ml/h) | $V_{max}$ (μg*ml/h*g BW) | $K_m$ (μg/ml) |
|---|---|---|---|---|---|
| Population mean | 0.072 | 0.0667 | 0.768 | 0.0276 | 0.892 |

TABLE 9-continued

Parameter estimates of the final PK-model for KIR-tgI mice.

| | $V_1$ (ml/g) | $V_2$ (ml/g) | $Q_{12}$ (ml/h) | $V_{max}$ (µg*ml/h*g BW) | $K_m$ (µg/ml) |
|---|---|---|---|---|---|
| % SE of mean | 6.1 | 10.7 | 44.4 | 2.1 | 9.1 |
| final SD | | | 36.7% | | |

Figure 10:
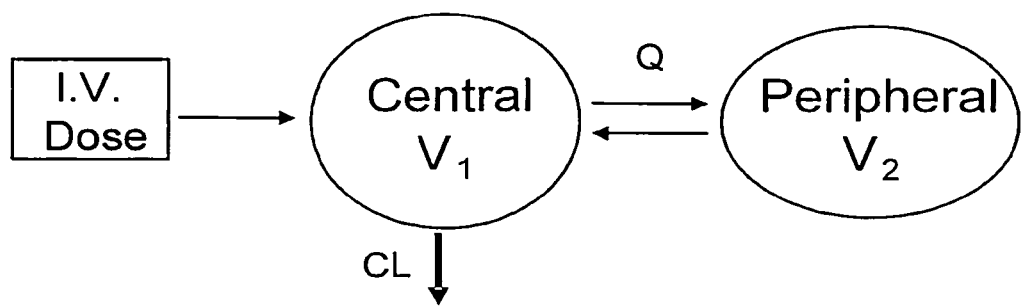
FIG. 10 shows a schematic representation of the two-compartment pharmacokinetic model applied for human PK predictions and for estimation of PK in cynomolgus monkeys.

No human PK data for Anti-KIR(1-7F9) were available but as Anti-KIR(1-7F9) is a fully human IgG4 it was expected that the antibody will display pharmacokinetic properties similar to an endogenous IgG4 in humans. It is well accepted that the PK-profile of IgG's which are not susceptible to target-mediated clearance generally may be described by a two-compartmental model, as shown in FIG. 10 (see Ghetie and Ward, Immunol Res 2002; 25:97-9113).

In order to predict the most likely human PK parameters for Anti-KIR(1-7F9), three different methods were compared as described in the following three sections.

(1) Typical PK Parameters for Human IgG

A wealth of information exists in the literature on PK of endogenous IgG's as well as monoclonal antibodies. A literature survey was conducted to identify typical values for the parameters (CL, V1, V2 and Q) defining the 2-compartment model for an IgG in humans. The PK parameters should be consistent with the general PK-features of a human IgG in humans. The initial central volume is approximately the plasma volume, i.e., 3 liters, the distribution volume is similar to or slightly larger than the central volume and an average terminal half-life is 20-23 days (Ghetie and Ward, Immunol Res 2002; 25:97-9113; Morell et al., J Clin Invest 1970; 49:673-80; Roskos et al., Drug Dev Res 2004; 61:108-20; Lobo et al., J Pharm Sci 2004; 93:2645-68).

These general features were combined with literature data on individual human and humanized antibodies from various literature sources. Generally, mAbs with documented target-mediated clearance or PK properties not consistent with endogenous IgG's have been excluded. The quoted clearance values are expected to reflect the general dose-independent clearance mechanism via the RES-system.

As expected, most mAbs have central volumes approximating the plasma volume (~40 ml/kg) and peripheral volumes of distribution are similar or slightly larger than this. The PK parameters used for the subsequent simulation of human PK are shown in Table 10. They were chosen as a reflection of both the general features and the specific parameters found during the literature survey. The terminal half-life using these parameters is 20 days.

TABLE 10

Predicted human PK parameters of Anti-KIR(1-7F9) based on typical IgG values

| PK parameter | Value |
|---|---|
| Clearance (CL) | 0.12 ml/h/kg |
| $V_1$ (central volume) | 40 ml/kg |
| $V_2$ (peripheral volume) | 40 ml/kg |
| Q (inter-compartmental clearance) | 1 ml/h/kg |

The parameter supported with least data is the inter-compartmental clearance, Q, for which it was necessary to use data from humanized and human antibodies with and without target mediated clearance. Where the micro-constants for transfer between the central and peripheral volumes were stated, Q was calculated as $V_1 \times k_{12}$ (rate constant for transfer between compartments 1 and 2). An inter-compartment clearance of 1 ml/h/kg and a central volume of 40 ml/kg are consistent with a distribution phase of 1-3 days, which is often observed for mAbs.

One of the important mechanisms regulating IgG plasma half-life in humans is binding to the human FcRn (Brambell) receptor (Lobo et al., J Pharm Sci 2004; 93:2645-68) and Anti-KIR(1-7F9) is expected to have similar affinity for the FcRn receptor as endogenous IgG4 antibodies.

Most known human or humanized monoclonal antibodies are of the IgG1 or IgG2-subtype. Anti-KIR(1-7F9) is an IgG4, but the PK parameters are expected to be similar to IgG1 and -2 as assessed by comparison of endogenous IgG-subclasses (Morell et al., J Clin Invest 1970; 49:673-80). Anti-KIR(1-7F9) is thus predicted to display PK-properties much like e.g. CP-675206, adalimumab, tefibazumab, pertuzumab and ABX-IL8 in humans.

With respect to monkey PK parameters, a previous NCA study showed that the AUC of anti-KIR(1-7F9) in cynomolgous monkeys was dose-linear in the investigated range 0.1-1 mg/kg.

For the population PK-model, a 2-compartment model was found to adequately describe the bi-exponential decline of plasma concentration following i.v. administration. No inter-individual variation on either of the four parameters was significant (on p-level<0.01). This was probably due to a high intra-individual variation, which was evident when plotting the actual plasma concentrations against time. The residual error in the model was acceptable (29%).

TABLE 11

Comparison of PK parameters for Anti-KIR(1-7F9) using NCA analysis and population PK methods.

| Method | $V_1$ (ml/kg) | $V_2$ (ml/kg) | CL (ml/h/kg) | Q (ml/h/kg) |
|---|---|---|---|---|
| NCA (mean values) | Vd = 276 | | 0.65 | — |
| Compartmental pop-PK | 62 | 181 | 0.64 | 3.8 |

$V_1$ = central volume, $V_2$ = peripheral volume of distribution, Vd = volume of distribution based on NCA, CL = clearance, Q = intercompartmental clearance.

As shown in Table 11, the NCA and population PK-model consistently show that the clearance of Anti-KIR(1-7F9) is somewhat higher (2-3 fold) compared to clearance reported for other human antibodies in monkeys. However, as the volume of distribution is also 2-3 fold higher, the terminal half-life (t½) was 8-11 days which is in accordance with expectations for a human antibody administered to monkeys (Halpern et al., Toxicol Sci 2006; 91(2):586-599; Gobburu et al., J Pharmacol Exp Ther 1998; 286(2):925-930). The exposure was observed to be dose-proportional and no indication of saturation mechanisms important for the clearance was observed.

Although some examples show that the monkey PK parameters may be directly transferable to humans, this should be done with caution as species differences in e.g. FcRn affinity may cause species differences in clearance (Lobo et al., J Pharm Sci 2004; 93:2645-68).

Allometric Scaling.

The four structural PK parameters obtained from population PK models (see above) in two species, i.e. mouse and monkey, (body weights of 0.025 and 2.5 kg), were used to perform allometric scaling to humans (70 kg). The PK parameter in question was plotted against body weight (BW). The obtained straight line determines A and B in the following equation (Lobo et al., J Pharm Sci 2004; 93:2645-

68; Tabrizi et al., "Pharmacokinetics and immunogenicity profiles for fully human monoclonal antibodies against soluble and membrane bound antigens in patients with psoriasis and melanoma," Poster on ASCPT 2004):

$$\text{Clearance} = A^*(\text{Body Weight})^B$$

All four parameters (CL, V1, V2, and Q) were calculated in a similar fashion. For scaling of volume of distribution, only V1 and V2 from the mouse model were considered. The third saturable compartment associated, e.g., with non-specific binding was disregarded since it is poorly documented for human PK of mAb's, which is believed to be linear, also for very small concentrations.

TABLE 12

Human PK parameters of Anti-KIR(1-7F9) predicted from allometric scaling

| PK parameter | Predicted human | Coefficients from allometric scaling | |
| --- | --- | --- | --- |
| | | A | B |
| Clearance (CL) | 0.46 ml/h/kg | −0.15 | 0.90 |
| V$_1$ (central volume) | 58 ml/kg | 1.8 | 0.98 |
| V$_2$ (peripheral volume) | 409 ml/kg | 2.15 | 1.25 |
| Q (inter-compartmental clearance) | 3.0 ml/h/kg | 0.61 | 0.93 |

Only a few examples exist of interspecies extrapolation of PK for mAbs using allometric scaling (Tabrizi et al., supra; Richter et al., Drug Metab Dispos 1999; 27:21-5, Lin et al., J Pharmacol Exp Ther 1999; 288(1):371-378). Generally, the prediction of human PK using this approach seems to work well although there seems to be an over-prediction of the clearance (Tabrizi et al., supra; Lin et al. supra). As was the case for ABX-IL8, only two species were used for the allometric scaling for Anti-KIR(1-7F9) and formally, the statistical basis for a straight line connecting two points is poor. However, including more species would not necessarily improve the prediction as a potential outlier from the relationship may not reflect the variability in the parameter but rather species differences in elimination mechanisms, particularly the affinity for the FcRn receptor. The affinity of Anti-KIR(1-7F9) for mouse and cynomolgus FcRn is unknown and thus the allometric scaling should be used with caution (Lobo et al., J Pharm Sci 2004; 93:2645-68).

In conclusion, on prediction of human PK, as Anti-KIR (1-7F9) is a fully human IgG it is expected that the antibody will display pharmacokinetic properties similar to endogenous IgG in humans. Based on allometric scaling and monkey clearance, the clearance in humans was estimated to be 0.46-0.64 ml/h/kg which is higher compared to typical values for clearance of human IgGs in humans (0.12 ml/h/kg). The literature prediction was used for development of a human PK-PD model as this approach estimated the lowest clearance and hence the highest potential exposure in humans.

PK/PD Model for KIR-Receptor Saturation in KIR-tgII Mice

Definition of PD Response Data (MFI).

An essential assumption for the present approach is that a reasonable value for % bound can be calculated/defined by median fluorescence intensity (MFI) data. Several different MFI measures have been used, for the control animals, and for the treated animals, both at screening, and at the time of measurement. These include:

MFI for Control Animals $MFI_{free.control}$: MFI associated with free receptors (PBMC)

$MFI_{max.bound.control}$: by incubating with 1-7F9, the max MFI associated with receptors bound to 1-7F9 (PBMC)

$MFI_{free.backgr}$: The background MFI when assessing free receptors $MFI_{bound.backgr}$: The background MFI when assessing bound receptors MFI for treated animals at screening $MFI_{free.screen}$: MFI associated with free receptors (PBMC) (only assessed for some animals)

MFI for Treated Animals at the Experimental Time Point $MFI_{free}$: MFI associated with free receptors (PBMC)

$MFI_{bound}$: MFI associated with bound receptors (PBMC)

$MFI_{bound.spleen}$: MFI associated with bound receptors (cells from spleen) (only assessed for some animals)

$MFI_{max.bound.spleen}$: MFI associated with bound receptors (cells from spleen) (only assessed for some animals)

Calculation of % Saturation of KIR-Receptors.

Using the control, the background, and the max bound in spleen, three normalized MFI values can be calculated for the treated animals:

$$MFI_{free.norm} = \frac{MFI_{free} - MFI_{free.backgr}}{\text{Mean}(MFI_{free.control}) - MFI_{free.backgr}} \quad \text{Eq. 1}$$

$$MFI_{bound.norm} = \frac{MFI_{bound} - MFI_{bound.backgr}}{\text{Mean}(MFI_{max.bound.control}) - MFI_{bound.backgr}} \quad \text{Eq. 2}$$

$$MFI_{bound.norm.owncontrol} = \frac{MFI_{bound.spleen} - MFI_{bound.backgr}}{\text{Mean}(MFI_{max.bound.spleen}) - MFI_{bound.backgr}} \quad \text{Eq. 3}$$

Under the assumption that the MFI increases linearly with the number of receptors involved, these normalized MFI values can be used to calculate % bound and % free receptors. A high variability was found in the individual MFI values for MFI.free.norm and MFI.bound.norm. Under the assumption that this variation is due to inter-individual variation in the number of KIR receptors, so that both MFI.free.norm and MFI.bound.norm is proportional to the number of KIR receptors, then % bound can be calculated as, $$\% \text{ bound} = \frac{MFI_{bound.norm}}{MFI_{bound.norm} - MFI_{free.norm}} \quad \text{Eq. 4}$$

which was the chosen method for the PK/PD-model.

For some animals, additional samples were taken to evaluate the MFImax.bound.spleen and MFI.bound.spleen, making it possible to use the animals own max level to normalize. For these animals it was possible to use MFI-.bound.norm.owncontrol to calculate % bound receptors. This approach was found to provide good agreement, except for the 15 min samples. This difference is considered likely to be due to the difference between PBMC and spleen cells, because anti-KIR(1-7F9) reaches the spleen later than it reaches the blood.

Modelling of % Bound.

A PK/PD-model was developed for describing the relationship between the plasma concentration of Anti-KIR(1-7F9) and the percentage receptor saturation in KIR-tgII mice. As the saturation was not in equilibrium with the plasma concentration at all time points, it was necessary to use a dynamic binding equation, linking the on- and off-rates ($k_{on}$ and $k_{off}$) at the receptor to the change in plasma concentration Cp with time. The equation to describe the total number of bound receptors B was:

$$\frac{dB}{dt} = k_{on}(B_{max} - B)C_p - k_{off}B \qquad \text{Eq. 5}$$

and equivalently we found the equation to describe the percent bound % B:

$$\frac{d\,\%\,B}{dt} = k_{on}(100 - \%\,B)C_p - k_{off}\,\%\,B \qquad \text{Eq. 6}$$

The dissociation constant, Kd, was calculated from the values of kon and koff obtained by the model via $Kd=k_{off}/k_{on}$.

When examining a plot of percent bound KIR-receptors versus plasma concentration at each time point, it appeared that at time points before 24 hours, less Anti-KIR(1-7F9) was needed for saturating the receptors than at later time points. Different empirical implementations of the apparent decrease of affinity demonstrated consistent results.

For the very low doses (≤0.0004 mg/kg), the plasma concentrations of Anti-KIR(1-7F9) were not measured as model predictions indicated that these would be around and below the limit of quantification. To include the measured % bound in the model, the PK part was extrapolated from higher doses. As a consequence of this extrapolation, the exact value of the highest, initial affinity, Kd1 is somewhat uncertain, and subsequently the final model used Kd1~0.004 µg/ml. Decreasing affinity was seen after 24-48 hours, with Kd2~0.1 µg/ml at late time points, where plasma concentrations were in the measurable range. Good agreement between the measured and modelled saturation could be obtained by the final approach. This final model can be written as, $$K_d = e^{\log(Kdmin)+(\log(Kdmax)-\log(Kdmin))\frac{Time}{(Time+T50)}} \qquad \text{Eq. 7}$$

with the parameter values given in Table 13, $k_{off}$ is kept constant, and $k_{on}$ is calculated as $k_{on}=k_{off}/Kd$. T50 is the time for 50% change of the Kd to occur.

As Anti-KIR(1-7F9) has two binding sites, the observed decrease in affinity has been interpreted as representing bivalent and monovalent binding modes or mixtures thereof. In several experimental settings, two different Kd-values for Anti-KIR(1-7F9) have been observed. Potential explanations for the change of binding mode from bivalent to monovalent in vivo could be reduced surface density of the KIR-receptors due to internalisation or other rearrangements of the receptors within the membrane resulting in more spacing between individual receptors. This would reduce the strong bivalent binding, as the probability of simultaneous engagement of both binding sites of an antibody depends strongly on the surface density and proximity of a membrane-bound target antigen (Larsson et al., Molecular Immunology 26, 735-739).

TABLE 13

Parameter estimates for the final PK/PD model in KIR-tgII mice

| Parameter | $k_{off}$ (1/h) | Minimal Kd (µg/ml) | $T_{50}$ (h) | Max. Kd (µg/ml) |
|---|---|---|---|---|
| Population mean | 0.607 | 0.004 | 72 | 0.1 |
| % SE of mean | 28.5 | Fixed | Fixed | Fixed |
| Residual error (% bound) Additive error model | | 13.3 | | |

Extrapolation of the Mouse PK/PD Model to Humans.

In NONMEM, the human PK/PD model was implemented by basically exchanging the mouse PK parameters in the NONMEM input file with the human PK parameters described in Table 12, while keeping the PD-structure of the input (Table 13). A range of doses and time points up to 13 weeks were simulated by means of this mode.

In the simulations, only population means of the structural parameters have been considered, i.e. no inter-individual or intra-individual variation of PK or PD parameters were included.

Figure 11:
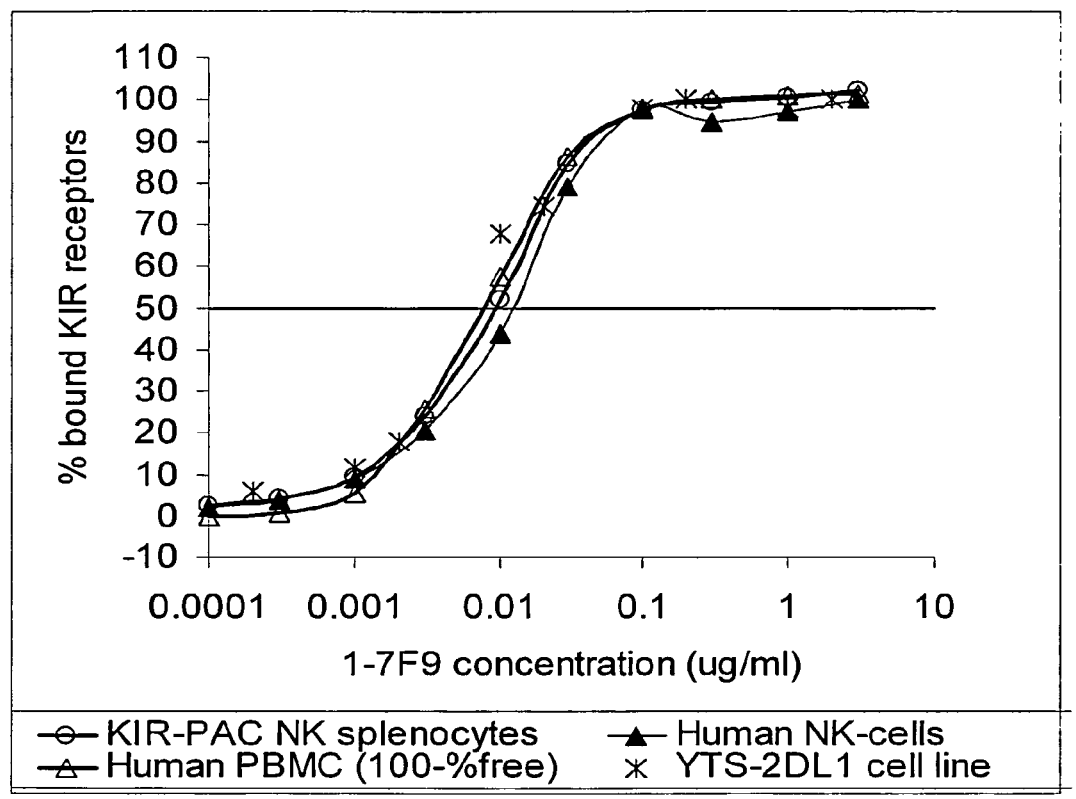
FIG. 11 shows parallel concentration versus occupancy curves by in vitro titration of Anti-KIR(1-7F9) binding to NK cells from KIR-tgII mice and to human NK cells at 37° C. Splenocytes from KIR-tgII mice and PBMC or NK cells from human donors, as well as the YTS cell line expressing KIR2DL1, were incubated with increasing concentrations of Anti-KIR(1-7F9) and then analysed by flow cytometry.

In vitro binding curves of various cell types from KIR-tgII mice and humans is shown in FIG. 11. These results support that the relationship between plasma concentration and saturation will be comparable in vivo for humans and KIR-transgenic mice. Thus, although the time course of plasma concentrations in humans will be different from that in mice, the PK/PD-model can be used to predict the saturation for a given plasma concentration in humans and at a given time point after dosage.

Similar in vitro-in vivo comparisons of affinities have been done successfully by comparing antiCD11a mAb hu1124 in chimpanzees and humans (Bauer et al., J Pharmacokinet Biopharm 1999; 27:397-420).

Application of the Final Model, Prediction of Maximal Saturation and Duration of Saturation.

The final predicted PK/PD model for Anti-KIR(1-7F9) in humans was used to perform simulations of percentage receptor occupancy versus time for different doses of Anti-KIR(1-7F9) in humans and deduce the maximum KIR-occupancy and duration of occupancy (Table 14). In order not to under-estimate potential activation, the model estimates were chosen to predict the maximal potential activation, i.e. the model is based on: 1) the highest potential exposure predicted from PK models, 2) a high affinity relationship between PK and saturation (low Kd), and 3) percent KIR occupancy as a measure of maximal potential activation of NK cells.

A dose predicted to cause detectable plasma concentrations of Anti-KIR(1-7F9) in humans as well as measurable but not full saturation was identified as 0.0003 mg/kg and suggested as the starting dose in the FHD trial.

TABLE 14

Predicted KIR-saturation on NK-cells, duration thereof and predicted plasma concentration in humans at different IV doses of Anti-KIR(1-7F9)

| Dose (mg/kg) | % saturated KIR receptors* | | No. of days >95% saturation | Plasma concentration of Anti-KIR(1-7F9) µg/ml | |
|---|---|---|---|---|---|
| | Max. bound | After 4 weeks | | $C_{max}$ | After 4 weeks |
| 0.0003 | 61 | <20 | 0 | 0.007 | 0.001 |
| 0.001 | 85 | <20 | 0 | 0.025 | 0.004 |

TABLE 14-continued

Predicted KIR-saturation on NK-cells, duration
thereof and predicted plasma concentration in humans
at different IV doses of Anti-KIR(1-7F9)

| Dose (mg/kg) | % saturated KIR receptors* | | No. of days >95% saturation | Plasma concentration of Anti-KIR(1-7F9) µg/ml | |
|---|---|---|---|---|---|
| | Max. bound | After 4 weeks | | $C_{max}$ | After 4 weeks |
| 0.01 | 98  | 37 | <1 | 0.25 | 0.04 |
| 0.1  | 100 | 85 | 9  | 2.5  | 0.4  |
| 0.3  | 100 | 95 | 25 | 7.4  | 1.3  |
| 1.0  | 100 | 98 | 56 | 25   | 4    |
| 1.5  | 100 | 99 | 63 | 37   | 6    |
| 3.0  | 100 | 99 | 84 | 74   | 12   |

*lower limit of quantification is estimated to be approximately 20% in the occupancy assay A simulation model has thus been developed to predict the relationship between dose of Anti-KIR(1-7F9), the resulting plasma concentration profile and the KIR-receptor occupancy in humans. This model was constructed by combining a typical PK model for IgG's in humans with a model for the relationship between plasma concentration and KIR-receptor occupancy. The latter model was developed using data from a KIR-tgII mouse study.

Cautious principles were used during model development, aiming at predicting the maximal potential occupancy. Based on this model, it was predicted that a dose of 0.0003 mg/kg is likely to produce a detectable (>20%), but not full saturation (<95%) in humans. This dose is expected to result in up to approximately 60% KIR occupancy at Cmax.

Example 7—Clinical AML Study

A single dose escalation trial is conducted in elderly AML patients (>60 years), who are in first complete remission following induction and consolidation chemotherapy, and not eligible for bone-marrow transplantation. A standard 3+3 design is applied, and a total of 7 dose levels are planned to be explored: Doses range from 0.0003 mg/kg to 3 mg/kg. Following dosing, the patients are monitored for safety, PK and KIR occupancy until KIR occupancy is no longer detectable.

An extension trial is also conducted. AML patients who have completed the dose-escalation trial and who are still in complete remission can participate in the extension trial, in which the patients can be dosed up to 6 times on a monthly basis. The patients are dosed with the same dose as they received in the previous trial.

Patients, Materials and Methods

In both trials, elderly AML patients (>60 years of age) in their first complete remission (CR) and not eligible for transplantation were eligible for the studies. At screening in the dose-escalation trial, the time since last dose of chemotherapy was at least 30 days and no more than 120 days. Other eligibility criteria included (but were not limited to) expression of KIR2DL1 and 2/3 on NK-cells, ECOG status 0-2 and recovery from all toxicities from previous treatment. For the extension trial, completion of the dose-escalation trial with an acceptable safety profile was an additional eligibility criterion.

Study Design

The dose-escalation trial is a multi-centre, open-label, single dose-escalation safety and tolerability trial. Seven dose levels are planned to be explored; 0.0003 mg/kg, 0.003 mg/kg, 0.015 mg/kg, 0.075 mg/kg, 0.3 mg/kg, 1 mg/kg and 3 mg/kg. A general (3+3) design is chosen for this trial. Each patient is allocated to one dose, and is monitored for safety, pharmacokinetics and pharmacodynamics until there is no detectable KIR-occupancy on the patients NK-cells. Safety, PK and KIR-occupancy are analysed on an on-going basis, and the data obtained during the first 4 weeks post dosing from each dose group generally forms the foundation of the dose-escalation decision.

The extension trial is designed as a repeated dosing, multi-centre, open-label, safety and tolerability. The dose given to the individual patient is the same as the patient received in the single dose trial. The patient can receive 6 administrations at 4 week interval i.e. 6 dosing cycles with a maximal to duration of 6 months. Each dosing cycle consists of a dosing visit and a safety monitoring visit. Following the last dosing, the patient is monitored for safety until there is no detectable KIR-occupancy on the patients NK-cells. The duration of this safety follow-up period likely depends on the dose received, and is expected to be maximally 24 weeks post the last dosing.

Safety (i.e. any observed toxicity) to Anti-KIR(1-7F9) administration is assessed using the US National Cancer Institute Common Terminology Criteria for Adverse Events (CTCAE) version 3.0. Pharmacokinetic endpoints, KIR-occupancy, markers of NK- and T-cell activation, WT-1 tumour marker, progression-free survival and overall survival is also evaluated.

Results

Based on the reported adverse events (AEs) and laboratory parameters, Anti-KIR(1-7F9) was well tolerated at the doses tested so far (0.0003 mg/kg, 0.003 mg/kg, 0.015 mg/kg). The SAEs reported in the trials so far have all been deemed to be unrelated or unlikely related to trial drug. Mild skin reactions (dorsal erythema, pruritus and cutaneous rash) of severity grade 1 occurring post dosing have been reported in 3 patients. These reactions were evaluated as non-serious and possibly related to trial drug, and the patients mostly recovered within a few days.

Example 8—Clinical Multiple Myeloma Study

A dose escalation trial is also conducted in patients with relapsed or refractory multiple myeloma (MMy), in which patients can be dosed 4 times on a monthly basis (i.e., a dosing interval of about 4 weeks). Eligible patients are 18 years or older.

A standard 3+3 design is applied, and a total of 7 dose levels are planned to be explored: Doses range from 0.0003 mg/kg to 3 mg/kg (0.0003 mg/kg, 0.003 mg/kg, 0.015 mg/kg, 0.075 mg/kg, 0.3 mg/kg, 1.0 mg/kg and 3.0 mg/kg). Following dosing, the patients are monitored for safety, PK and KIR occupancy until KIR occupancy is no longer detectable.

Example 9—Pharmacokinetics in Patients

Method

Plasma concentrations of anti-KIR (1-7F9) are determined by ELISA as briefly described below.

The plates are coated with KIR2DL3 coating solution (100 µl/well) and incubated overnight at about +4° C. The plates are then washed 3 times with wash buffer using an automated plate washer (400 µl/well). Blocking buffer is added (200 µl per well) and plates are incubated for approximately 2 hours on a plate shaker at room temperature. After this, the plates are once again washed 3 times with wash buffer (400 µl/well).

Standards, quality controls and samples are added to the plates (100 μl/well) before incubation for approximately 2 hours on the plate shaker at room temperature. Before adding mouse anti-human IgG4:peroxidase working solution (100 μl/well) the plates are washed another 3 times (as above). The plates are then again incubated for approximately 2 hours on a plate shaker at room temperature, after which they are washed once again.

TMB is added to the plates (100 μl/well), which are then incubated for approximately 30 minutes on a plate shaker at room temperature. The enzymatic reaction is terminated with addition of stop solution (50 μl/well). Absorbances are read at 450 nm (reference filter 650 nm).

The lower limit of quantification for this study is 5.000 ng/mL and the upper limit of quantification for this study is 110.0 ng/mL.

Results

Figure 12:
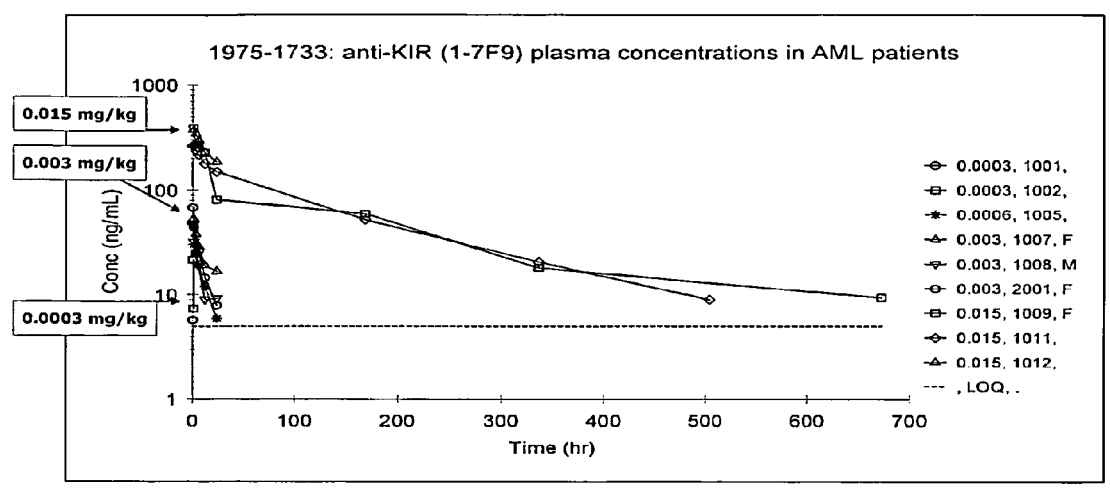
FIG. 12 shows Anti-KIR(1-7F9) plasma concentrations in AML patients versus time after administration.

So far, three dose levels of 0.0003, 0.003 and 0.015 mg/kg of anti-KIR mAb have been administered intravenously to nine AML patients in the dose-escalation trial, while 0.0003 mg/kg anti-KIR has been administered to four MMy patients. From the plasma data obtained in AML patients to date, there appears to be a dose linear increase in exposure between the three lowest doses (FIG. 12). The concentrations observed in the MMy patients align well with those of the AML patients. After the 0.015 mg/kg dose, measurable anti-KIR plasma concentrations have been detected for up to four weeks after dose administration. The highest plasma exposure recorded so far approximates 400 ng/mL after the 0.015 mg/kg dose.

Example 10—KIR Occupancy Assay

In this assay, receptor occupancy is evaluated on human whole blood samples by four-color fluorescence analysis. Briefly, free and bound KIR2D receptor levels are assessed on T and NK lymphocytes in EDTA anti-coagulated peripheral blood. Free site assay will assess unbound KIR2D by staining with PE-conjugated 1-7F9, which binds to the KIR2D molecule. Bound site assay will assess KIR2D receptors occupied by 1-7F9 by staining with a PE-conjugated mouse anti-human IgG4 monoclonal antibody that recognizes the 1-7F9 bound to the KIR2D receptors. The Free and Bound Assays will allow for assessment of both percentage positive staining as well as the fluorescence intensity [MESF] for 1-7F9-PE or anti-hIgG4-PE. The following combinations of conjugated antibodies are used in the following two assays:

Free Site Assay: CD3/1-7F9/CD45/CD56
Bound Assay: CD3/☐hIgG4/CD45/CD56

Samples are analyzed on a Becton Dickinson FACScalibur using the Becton Dickinson Cellquest software. T cells are defined as CD45+CD3+ lymphocytes and NK cells are defined as CD45+CD3−CD56+ cells.

Example 11—Translation of PK/PD Model into Humans

Data from three on-going clinical trials with 1-7F9 (see Examples 7 and 8) was used to validate and update the preclinical PK/PD model described in Example 6, using pharmacokinetic and KIR-occupancy data obtained as described in Examples 9 and 10.

As described in Examples 7 and 8, patients have received an i.v. dose of 0.0003, 0.003 or 0.015 mg/kg body weight. Some patients have received repeated doses at the same dose level with 4 weeks' interval, but for the purposes of the following calculations, these doses have been treated as independent, single doses, as no or limited effect on the occupancy carries over between dosing events at these low doses.

Calculation of Occupancy

For calculation of KIR occupancy, it was not necessary to use the complex formula used in the preclinical PK/PD model, as each patient served as his/her own control. Also, only the assay assessing the number of free KIR receptors was used as the validation indicated this assay to be more robust. The standardized fluorescence expressed as Molecules of Equivalent Soluble Fluorochrome (MESF) values (MESF) of NK-cells were used for the calculation:

$$\% \text{ free} = 100\% \times \frac{MESF}{MESF_{predose}} \qquad \text{Eq. 8}$$

$$\% \text{ occupancy} = 100\% - \% \text{ free} \qquad \text{Eq. 9}$$

Occupancy values below 0 were per definition set to 0. To account for day-to-day variability in the assay, the cut-off for significant KIR-occupancy was set to 30%.

Data Analysis

The PK and PD data from the trials were subjected to an exploratory analysis, plotting KIR occupancy vs. plasma concentration of 1-7F9 and observing any trends in the data. For illustrative purposes, a simple monovalent binding isoterm were overlaid on these plots. From the preclinical model, it was known that it is reasonable to assume that the affinity (Kd) is constant within a certain time frame and, hence, KIR occupancy for each time frame was calculated using Eq. 10:

$$\% \text{ occupancy} = 100\% \times \frac{(1 - 7F9 \text{ plasma } conc.)}{(Kd + 1 - 7F9 \text{ plasma } conc.)} \qquad \text{Eq. 10}$$

This also implied that the binding could be assumed to be in instantaneous equilibrium with the plasma concentration. From the preclinical PK/PD-model, this was known to a reasonable assumption.

In addition, some of the PK and PD parameters predicted by the preclinical PK/PD model were compared to the actual observations during the on-going clinical trials.

Population PK

The available PK data were used for population modelling to generate a preliminary PK-model for 1-7F9 in humans, while the PK/PD relationship was based on the exploratory analysis.

Software.

The following software was used for final data file generation:
S-plus, version 6.1, Insightful Corporation, Seattle, Wash., USA.

The following software was used for nonlinear mixed-effects modelling:
Compaq Visual Fortran, version 6.6a, Hewlett-Packard Company, Palo Alto, Calif., USA.
NONMEM V, version 1.1, GloboMax, Hanover, Md., USA.
Visual-NM, version 5, RDPP, Montpellier, France.

Installation/validation of the software was carried out in the following way:
NONMEM functionality was verified using current departmental procedures.

Other software was installed as recommended by the manufacturers.

MODEL DEVELOPMENT: NONMEM's first order conditional (FOCE) estimation method with interaction was used for model development. Evaluation of and discrimination between intermediate models were based on objective function values and standard graphical evaluation methods.

In terms of objective function value, changes in this value were assumed to be $\chi^2$-distributed (for nested models), and criteria for expanding the model were defined and used accordingly.

Handling of Values Below LOQ:

Values below LOQ were excluded from the modelling, but the time point was kept in the data file so as to obtain a predicted value.

Structural Models and Error Models.

Proportional as well as combined error models were investigated for intra-individual variability.

Checking Procedures.

The final model (i.e. NONMEM control stream) was thoroughly proof-read to ensure correctness.

Covariate Analysis.

No covariate analysis was performed due to the low number of few patients.

Evaluation Procedures.

Evaluation of the final model was performed by means of standard graphical evaluation methods.

Structural Models:

Standard one and two-compartment models were investigated. In addition, models including saturable clearance and/or distribution were tested.

Results

Predictive Value of the Preclinical PK/PD Model.

The plasma concentration of 1-7F9 immediately (10 min.) after intravenous administration was accurately predicted with the PK-model using generic human IgG parameters, cf. table 15. The maximal plasma concentration is primarily related to the size of the central volume, which is fairly well-defined for human beings, so it is expected that this parameter would be the one which is predicted with greatest certainty. For predictions at later time points, the kinetic processes (clearance, distribution) are at play and thus less certain predictions can be expected, as observed, cf. below.

TABLE 15

Plasma concentration of 1-7F9 in humans 10 min. after i.v. administration of the doses listed.

| Dose | Predicted | Observed | |
|---|---|---|---|
| mg/kg | ng/ml | Mean (sd) | n |
| 0.0003 | 7.5 | 11 (7) | 5* |
| 0.003 | 75 | 56 (11) | 3 |
| 0.015 | 370 | 344$ (66) | 3 |

"Predicted" is the value predicted by the preclinical PK/PD model,
"Observed" are actual mean (standard deviations) values from the clinical trials.
n is the number of data points.
*Two LOQ values not included,
$1 h time point used,
10 min. not determined.

Likewise, the maximal occupancy (2 hours post-dose) was well predicted by the model (Table 16). Given that the plasma concentration as well as the KIR-occupancy at approximately the same time point were both well predicted, it may be concluded that the high initial affinity included in the preclinical PK/PD model was indeed suitable for predicting KIR occupancy at early time points post-dose in humans.

TABLE 16

KIR occupancy (%) in humans 2 hours after i.v. administration of the 1-7F9 doses listed.

| Dose | Predicted | Observed | |
|---|---|---|---|
| mg/kg | % | Mean (sd) | n |
| 0.0003 | 62 | 53 (20) | 10 |
| 0.003 | 95 | 93 (2) | 7 |
| 0.015 | 99 | 94 (1) | 3 |

"Predicted" is the value predicted by the preclinical PK/PD model,
"Observed" are actual mean (standard deviations) values from the clinical trials.
n is the number of data points.
For technical reasons, maximally 95% could be detected in the assay.

Figure 13:
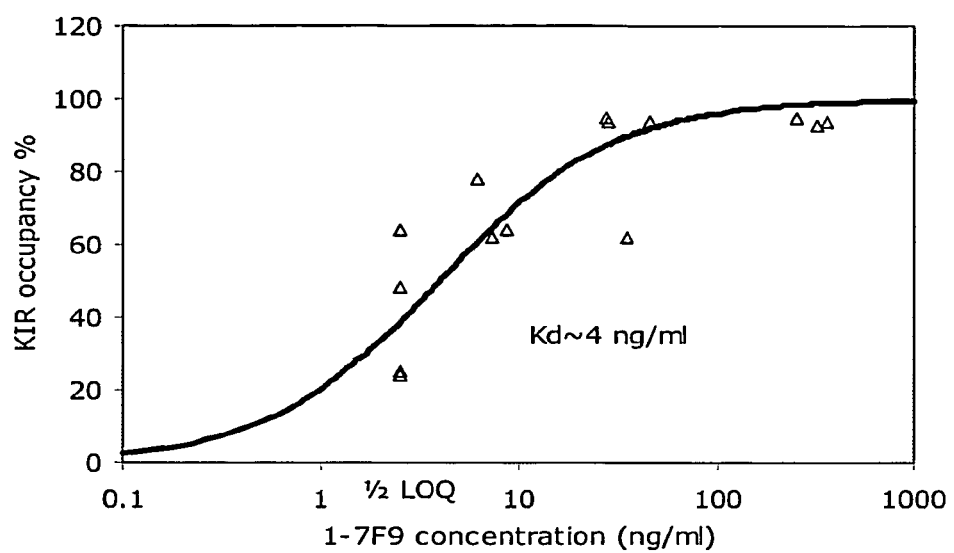
FIG. 13 shows the relationship between KIR occupancy 2 hours post-administration and serum concentration of 1-7F9 in humans. Plasma concentrations below Limit of Quantification (LOQ) have been plotted at ½ LOQ (2.5 ng/ml). The solid line is not a fit to the actual data, but a fit of a monovalent saturation isotherm with Kd=4 ng/ml (Eq. 10).
Figure 14:
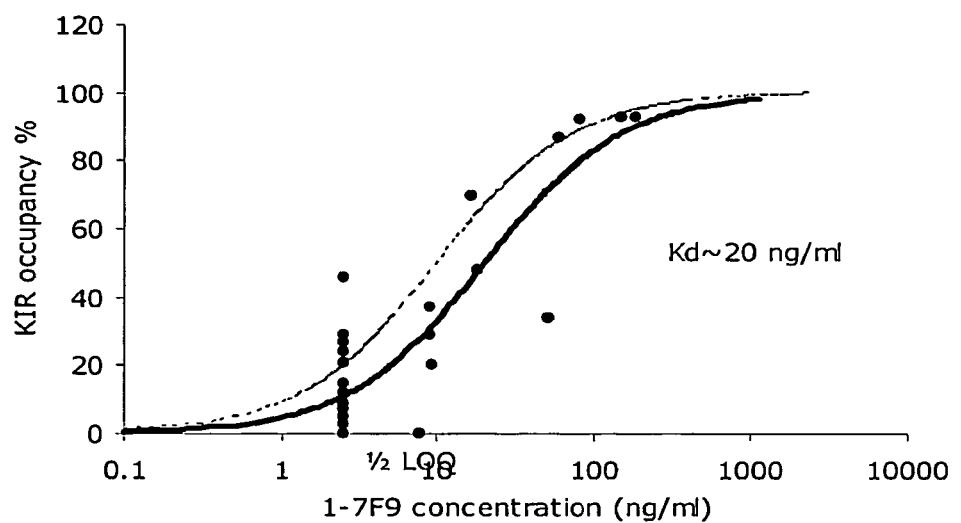
FIG. 14 shows the relationship between KIR occupancy for time points 24 hours up to 6 weeks post-administration, and serum concentration of 1-7F9 in humans. Values below LOQ have been plotted at ½ LOQ (2.5 ng/ml). The solid line is not a fit to the actual data, but a fit of a monovalent saturation isotherm with Kd=20 ng/ml (Eq. 10). The dotted line shows Kd=9 ng/ml (predicted for 24 h).

The initial KIR affinity in humans could only be approximated from the data, as the 1-7F9 plasma concentration for many data points was below LOQ. However, the occupancy data indicated that the initial affinity was close to the predicted one of 4 ng/ml, as seen in FIG. 13, depicting the KIR occupancy 2 hours post-dose vs. the plasma concentration of 1-7F9. The preclinical PK/PD model predicted that the affinity would decrease over time. Although only based on few data points so far, such a trend was indeed observed for the occupancy data obtained from 24 hours post-dose and up to 6 weeks (FIG. 14). A tentative fit with a Kd of 20 ng/ml has been superimposed on the plot. The preclinical model predicted the Kd at 24 h to be 9 ng/ml, also shown in the plot.

The first few days post-dose, the time course of KIR receptor desaturation was well described by the preclinical PK/PD model. The moderate deviation at subsequent time points, was probably due to the plasma concentration decreasing somewhat faster than expected from the generic IgG PK parameters used to predict the human PK. Nevertheless, for maximal occupancy, the underlying plasma concentration was well predicted by the model.

Population PK Model.

As expected for a monoclonal antibody, the time course of plasma concentration followed a bi-exponential pattern. Thus, a two-compartment model gave a better fit to data better than a one-compartment model.

A trend for non-dose proportionality in the distribution phase was seen, with lower doses being distributed more rapidly than the high dose. The PK parameters for this updated model are shown in Table 17.

TABLE 17

Mean population PK parameters from preliminary population PK model based on data from the first three dose levels of the clinical trial.

| PK parameter | Value |
|---|---|
| Clearance (CL) | 0.49 ml/h/kg |
| $V_1$ (central volume) | 47 ml/kg |
| $V_2$ (peripheral volume) | 69 ml/kg |
| Q (inter-compartmental clearance)* | 1.5 ml/h/kg |

*Q is shown for the 0.015 mg/kg dose level only

From the data obtained so far, the clearance seemed to be higher (about 4 times) than the generic one for human IgGs of 0.12 ml/h/kg used in the preclinical PK/PD model. Without being bound by theory, this discrepancy could suggest that 1-7F9 undergoes target-mediated disposition, as has often been observed for antibodies binding membrane-bound targets, and might imply that the clearance of 1-7F9 could be saturable at higher doses, hence resulting in a longer terminal half-life. The same considerations hold for the volume of distribution, which could be slightly higher than predicted. However, as also indicated by the exploratory analysis above, the size of the central volume of distribution was quite well predicted (0.047 vs 0.04 l/kg).

Conclusions

Overall, the features predicted by the preclinical PK/PD model were also observed in the clinical data obtained so far. The maximal occupancy as well as the maximal 1-7F9 plasma concentration were well predicted. The affinity may change with time, as was also predicted by the model.

Example 12—Dosing Regimens Based on Updated PK/PD Model

The PK parameters obtained as described in the previous Example were applied to determine the optimal dosing frequency for the Anti-KIR(1-7F9) dose levels to be used in the clinical trials.

The dosing frequency in clinical therapy using 1-7F9 depends on the steady state plasma concentration needed for saturation as well as the clearance and volume of distribution of 1-7F9.

Although the maximal occupancy is initially governed by the high affinity (preliminary results indicate about 4 ng/ml), the plasma concentration needed subsequently to maintain the saturation is higher (preliminary results suggest about 20 ng/ml).

The concentration needed to obtain >95% occupancy, here termed SatConc, is approximately 20 times higher than the Kd for binding (cf. Eq. 10). For determination of dosing intervals, it was assumed that the plasma concentration should be above SatConc at all times within the intervals in order to maintain KIR occupancy >95%.

The calculation of dosing intervals was based on Eq. 11 (Gabrielsson J & Weiner D, Pharmacokinetic and pharmacodynamics data analysis. 3$^{rd}$ Ed. Taylor & Francis 2000):

$$D = \frac{SatConc \times V_d}{e^{-tau \times Cl/Vd}} \qquad \text{Eq. 11}$$

where $V_d$ is volume of distribution at steady state (V1+V2 in table 17), D is the dose, Cl=clearance and tau=dosing interval. By rearrangement, tau may be found as $$tau = \frac{-\ln(SatConc \times V_d)}{Cl/V_d} \qquad \text{Eq. 12}$$

Tau was determined for the doses above 0.015 mg/kg using the PK parameters from Table 17 and SatConc=400 ng/ml. For the lower doses, Eq. 12 could not be used as it was based on the lower Kd being manifest 24 h post-dose. Instead, the dosing intervals were approximated by extrapolation and staggering of the data and assuming that the affinity will remain at its initial high affinity with repeated dosing, which may or may not be the case. The results are shown in Tables 18 and 19.

TABLE 18

Predicted dosing regimens for doses used in the clinical trials, aiming at >95% KIR occupancy at steady-state (except 0.0003 mg/kg)

| Dose (mg/kg) | Observed single dose duration of >95% occupancy (days) | Predicted SS duration of 95% occupancy (tau) $ (weeks) | Dosing regimen |
|---|---|---|---|
| 0.0003 | <0.5 | | 2-3x/day* |
| 0.003 | <7 days | | 1-2x/day* |
| 0.015 | 2-7 days | | 3-5x/week* |
| 0.075 | — | 0.7 | 1-2x/week |
| 0.3 | — | 2.6 | 1x/2 weeks |
| 1 | — | 4.3 | 1x/4 weeks |
| 3 | — | 5.9 | 1x/6 weeks |

*based on observed data, not based on model prediction.
$ SS is predicted steady state using the updated PK-model
$$ For feasibility of implementation, tau was rounded up the nearest value of whole days or weeks, as appropriate.

TABLE 19

Predicted dosing regimens for doses used in the clinical trials, aiming at >95% KIR occupancy at steady-state. Dosing frequencies stated per weeks and months.

| Dose (mg/kg) | Dosing interval if hitting exactly 95% at C$_{min}$ | | Dosing frequency, whole weeks and months | | | |
|---|---|---|---|---|---|---|
| | tau (days) | tau (weeks) | Pr. week | Pr. 2 weeks | Pr. month (4.3 weeks) | Pr. two months (8.6 weeks) |
| 0.075 | 5 | 0.7 | 1.4 | 2.9 | 6.1 | 12 |
| 0.3 | 18 | 2.6 | 0.4 | 0.8 | 1.7 | 3.3 |
| 1 | 30 | 4.3 | 0.2 | 0.5 | 1.0 | 2.0 |
| 3 | 41 | 5.9 | 0.2 | 0.3 | 0.7 | 1.5 |

The calculations are based on assumptions of dose-linear PK parameters. Alternatively, the dose giving KIR-saturating plasma levels may instead be found using simulations from a (population) PK/PD model including any observed non-linearities.

Example 13—Anti-KIR Mediated Activation of NK-Cells in Human Cancer Patients

Upon NK- and T-cell mediated killing of tumor cells, the lysosomal-associated membrane protein-1 (LAMP-1 or CD107a) lining the membrane of cytolytic granules, is exposed on the NK- and T-cell surface (Betts at al., J Immunol Methods 2003; 281:65-78). In clinical trials, assessments of CD107a expression on NK-cells have been shown to be a feasible and reliable marker of NK-cell mediated killing of tumor cells (Koch et al, Ann Surg 2006; 244:986-92).

In the on-going clinical trials investigating Anti-KIR treatment of patients with AML, CD107a was assessed by flow cytometry. Blood samples were collected, red blood cells were lysed, and peripheral blood cells were washed and subsequently stained with antibodies against CD3, CD45, CD56, and CD107a. Data were acquired on a BD FACScanto with BD FACSDiva software.

Figure 15:
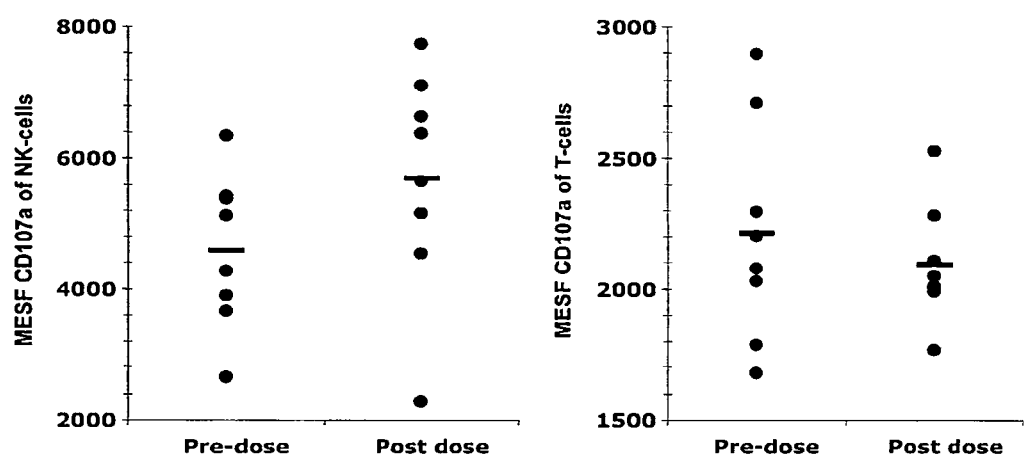
FIG. 15 shows the levels of CD107a on NK- and T-cells in patient blood after administration of Anti-KIR(1-7F9), where CD107a levels were increased on NK-cells 24 h post-administration.

The results showed a clear up-regulation of CD107a on NK-cells but not T-cells. In a total of 6 out of 8 patients treated with a single Anti-KIR(1-7F9) dose (0.0003, 0.003 and 0.015 mg/kg), CD107a levels were increased on NK-cells 24-hours post-dosing (FIG. 15).

Moreover, in AML patients treated with multiple cycles of Anti-KIR(1-7F9) (same doses as above, given up to a maximum of 6 repeated doses), increased levels of CD107a were observed after repeated dosing. By ex vivo stimulation of patient NK-cells with tumor cells, the increased levels of CD107a coincided with increased killing of tumor cells. In patients with multiple myeloma, upregulation of CD107a upon Anti-KIR(1-7F9) dosing was observed in a total of 4 out of 5 patients.

In addition to CD107a, MIP-1β (macrophage inflammatory protein-1beta) has also been shown to be a robust marker of NK-cell activation and a potent NK-cell chemoattractant and stimulant of NK-cell mediated anti-tumour effects (Hanna et al., J Immunol 2004; 173:6547-63; Luo et al., Cell Mol Immunol. 2004; 1:199-204). Upon 1-7F9 administration, increased serum levels of MIP-1β was observed in a total of 11 out of 12 patients across trials in AML and multiple myeloma.

Collectively, these results demonstrated that Anti-KIR treatment of cancer patients rapidly and repeatedly enables NK-cell activation and killing of tumor cells.

Example 14—Anti-KIR Mediated Reduction of Tumor Markers

In acute myeloid leukaemia (AML), detection of minimal residual disease is of growing importance for risk stratification and early detection of relapse. The Wilms' tumour gene 1 (WT-1) transcript has been shown to be overexpressed in more than 90% of myeloid leukemias. WT-1 correlates well with tumour burden and has proven to be a valuable tool for molecular monitoring response to treatment in AML. Furthermore, increases in WT-1 levels precedes clinical relapse (Cilloni et al., Acta Haematol. 2004; 112: 79-8)

In the on-going clinical trials investigating Anti-KIR(1-7F9) treatment of patients with AML, WT-1 levels were measured in bone marrow and in blood samples. WT-1 levels were assessed by a qRT-PCR assay (PQPP-01) from Ipsogen according to the manufacturers instructions. Upon Anti-KIR(1-7F9) dosing, a drop in either bone marrow or blood WT-1 levels has been observed in a total of 4 out of 6 patients.

Multiple myeloma is a malignant B-cell disorder characterized by a monoclonal expansion of malignant plasma cells in the bone marrow. A hallmark of the disease is high levels of monoclonal (M) immunoglobulin (M-protein) in the serum and/or urine. In clinical trials, routine monitoring of M-protein as a marker of response to treatment is a standard clinical practice (Prince et al., Leuk Lymphoma. 2007; 48:46-55).

In the on-going clinical trial investigating Anti-KIR(1-7F9) treatment of patients with multiple myeloma, urine M-protein was assessed by a gel electrophoresis assay (3398) from Helena Laboratories according to the manufactures instructions. Reduction of urine M-protein upon Anti-KIR dosing was observed in a total of 2 out of 4 evaluable patients.

Collectively, these results demonstrate that Anti-KIR(1-7F9) treatment of cancer patients was able to induce an anti-tumor response.

Example 15—Formulation Study

In this example we have tested 5 different 1-7F9 formulations in a 6-month stability setup.

Materials and Methods

Five different formulations of 1-F79 (10 mg/mL 1-7F9, 10-50 mM sodium phosphate, 160-240 mM sucrose, 0.1-0.5 mg/ml Polysorbate 80, at pH 7.0) were analyzed based on pH, appearance, GP HPLC, SDS-PAGE, and IEF, over a storage period of up to six months at three different temperatures, according to the schedule in Table 20. Details on the formulations are provided in Table 21.

The analyses were performed essential as described in Example 3, except that Gel permeation GP HPLC was carried out on an Waters 2695 system and the mobile phase was 0.1 M sodium phosphate at pH 7.0 at a flow rate of 1.0 mL/min. Circular Dichroism was done on a Chirascan CD (Applied Photophysics).

TABLE 20

Schedule for second formulation study

| | Time point (months) | | | | |
|---|---|---|---|---|---|
| Temperature | 0 | 1 | 2 | 3 | 6 |
| 5° C. | X | NT | X | X | X |
| 25° C. | X | X | NT | X | X |
| 40° C. | X | X | X | X | NT |

X = tests performed;
NT = not tested

TABLE 21

Formulations tested

| | Amount | | | | |
|---|---|---|---|---|---|
| Ingredient | Formulation 1 | Formulation 2 | Formulation 3 | Formulation 4 | Formulation 5 |
| Anti-KIR | 10 mg/ml | 10 mg/ml | 10 mg/ml | 10 mg/ml | 10 mg/ml |
| Sodium phosphate monobasic | 1.38 mg/ml (10 mM) | 2.76 mg/ml (20 mM) | 4.14 mg/ml (30 mM) | 6.90 mg/ml (50 mM) | 2.76 mg/ml (20 mM) |
| Sucrose | 82.2 mg/ml (240 mM) | 75.3 mg/ml (220 mM) | 68.5 mg/ml (200 mM) | 54.8 mg/ml (160 mM) | 75.3 mg/ml (220 mM) |
| Tween80 | 0.1 mg/ml | 0.1 mg/ml | 0.1 mg/ml | 0.1 mg/ml | 0.5 mg/ml |
| pH | 7.0 | 7.0 | 7.0 | 7.0 | 7.0 |

Results

The results are shown in Tables 22A-C, 23A-C, 24A-C, and 25A-C.

TABLE 22 pH measurements

A - 5° C.

| | Month | | |
|---|---|---|---|
| | 0 | 3 | 6 |
| Formulation 1 | 7.03 | 7.06 | 7.06 |
| Formulation 2 | 7.04 | 7.04 | 7.03 |
| Formulation 3 | 7.05 | 7.03 | 7.01 |
| Formulation 4 | 7.05 | 7.03 | 7.00 |
| Formulation 5 | 7.05 | 7.02 | 7.02 |

B - 25° C.

| | Month | | | |
|---|---|---|---|---|
| | 0 | 1 | 3 | 6 |
| Formulation 1 | 7.03 | 7.08 | 7.06 | 7.05 |
| Formulation 2 | 7.04 | 7.07 | 7.05 | 7.03 |
| Formulation 3 | 7.05 | 7.06 | 7.02 | 7.01 |
| Formulation 4 | 7.05 | 7.05 | 7.03 | 7.00 |
| Formulation 5 | 7.05 | 7.04 | 7.03 | 7.02 |

C - 40° C.

| | Month | | |
|---|---|---|---|
| | 0 | 1 | 3 |
| Formulation 1 | 7.03 | 7.07 | 7.06 |
| Formulation 2 | 7.04 | 7.04 | 7.04 |
| Formulation 3 | 7.05 | 7.02 | 7.03 |
| Formulation 4 | 7.05 | 7.02 | 7.02 |
| Formulation 5 | 7.05 | 7.01 | 7.05 |

TABLE 23

Appearance.

A - 5° C.

| | Month | | |
|---|---|---|---|
| | 0 | 3 | 6 |
| Formulation 1 | 2 | 2 | 2 |
| Formulation 2 | 2 | 2 | 2 |
| Formulation 3 | 2 | 2 | 2 |
| Formulation 4 | 2 | 2 | 2 |
| Formulation 5 | 2 | 2 | 2 |

B - 25° C.

| | Month | | |
|---|---|---|---|
| | 0 | 3 | 6 |
| Formulation 1 | 2 | 2 | 2 |
| Formulation 2 | 2 | 2 | 2 |
| Formulation 3 | 2 | 2 | 2 |
| Formulation 4 | 2 | 2 | 2 |
| Formulation 5 | 2 | 2 | 2 |

TABLE 23-continued

Appearance.

C - 40° C.

| | Month | | | |
|---|---|---|---|---|
| | 0 | 1 | 2 | 3 |
| Formulation 1 | 2 | 2 | 2 | 2 |
| Formulation 2 | 2 | 2 | 2 | 2 |
| Formulation 3 | 2 | 2 | 2 | 2 |
| Formulation 4 | 2 | 2 | 2 | 2 |
| Formulation 5 | 2 | 2 | 2 | 2 |

Scoring: 0 being worst; 1 indicating a formulation with possibly suitable properties for a pharmaceutical product; and 2 indicating a formulation of high quality, suitable for a pharmaceutical product.

TABLE 24

Purity by GP-HPLC, determined as percent monomer.

A - 5° C.

| | Month | | |
|---|---|---|---|
| | 0 | 3 | 6 |
| Formulation 1 | 94 | 94 | 95 |
| Formulation 2 | 94 | 95 | 94 |
| Formulation 3 | 94 | 95 | 95 |
| Formulation 4 | 94 | 95 | 93 |
| Formulation 5 | 94 | 94 | 94 |

B - 25° C.

| | Month | | | |
|---|---|---|---|---|
| | 0 | 1 | 3 | 6 |
| Formulation 1 | 94 | 93 | 94 | 91 |
| Formulation 2 | 94 | 94 | 94 | 91 |
| Formulation 3 | 94 | 93 | 94 | 91 |
| Formulation 4 | 94 | 93 | 94 | 91 |
| Formulation 5 | 94 | 94 | 94 | 89 |

C - 40° C.

| | Month | | | |
|---|---|---|---|---|
| | 0 | 1 | 2 | 3 |
| Formulation 1 | 94 | 89 | 82 | 74 |
| Formulation 2 | 94 | 89 | 82 | 76 |
| Formulation 3 | 94 | 88 | 83 | 76 |
| Formulation 4 | 94 | 86 | 79 | 74 |
| Formulation 5 | 94 | 91 | 80 | 74 |

TABLE 25

Bioactivity (arbitrary units)

| | Month | | |
|---|---|---|---|
| A-5° C. | 0 | 3 | 6 |
| Form. 1 | 8.78 | 8.19 | 8.70 |
| Form. 2 | 8.88 | 9.99 | 10.10 |
| Form. 3 | 9.48 | 9.38 | 9.30 |
| Form. 4 | 9.57 | 9.45 | 8.00 |
| Form. 5 | 9.91 | 9.50 | 8.60 |

TABLE 25-continued

| | Bioactivity (arbitrary units) | | | |
|---|---|---|---|---|
| | Month | | | |
| B-25° C. | 0 | 1 | 3 | 6 |
| Form. 1 | 8.78 | 8.90 | 8.60 | 7.50 |
| Form. 2 | 8.88 | 9.46 | 7.99 | 7.00 |
| Form. 3 | 9.48 | 9.32 | 8.56 | 7.30 |
| Form. 4 | 9.57 | 9.30 | 9.28 | 7.20 |
| Form. 5 | 9.91 | 10.11 | 9.00 | 8.20 |

| | Month | | | |
|---|---|---|---|---|
| C-40° C. | 0 | 1 | 2 | 3 |
| Form. 1 | 8.78 | 7.29 | 5.80 | 4.47 |
| Form. 2 | 8.88 | 7.74 | 5.70 | 4.39 |
| Form. 3 | 9.48 | 6.53 | 4.96 | 3.71 |
| Form. 4 | 9.57 | 6.27 | 5.27 | 3.75 |
| Form. 5 | 9.91 | 6.14 | 6.15 | 4.42 |

After 6 months, no substantive differences could be observed between the five different formulations, in that they were all shown to be of high quality, suitable for a pharmaceutical antibody product, and showed no substantial differences when analyzed by pH, Appearance, GP-HPLC, Bioactivity. No differences could be detected by Circular Dichroism either. Further, even though the Polysorbate 80 concentrations tested in this experiment (0.010-0.050%) were 10 to 50 times higher than in the previous setup, no real influence of the actual polysorbate concentration on the parameters tested could be detected. A formulation comprising 20 mM sodium phosphate, 220 mM sucrose, 0.001% Polysorbate 80, at pH 7.0, however, had the advantage of having both a low phosphate content and correct osmolarity, in addition to excellent stability properties.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Moreover, the use of the term "about" in any group of values is intended to provide support for each value in such group (regardless of inconsistencies in such usage herein) unless otherwise indicated (e.g., the phrase about 1, 2, or 3 should be interpreted as providing support for "about 1," "about 2", and "about 3").

Recitation of ranges of values herein are merely intended to serve as a shorthand method of referring individually to each separate value falling in the range that is within the same order of magnitude and same level of significance (i.e., all similarly significant figures as the lower end point of the range, unless otherwise indicated herein, and each separate value is incorporated into the specification as if it were individually recited herein. Thus, for example, a range of 1-100 herein provides support for each integer between (and including) 1-100 (i.e., 1, 2, 3, 4, . . . 98, 99, and 100) and a range of 0.1-1 provides support for each value in the same order of magnitude and level of significance as 0.1 between and including these endpoints (i.e., 0.1, 0.2, 0.3, . . . 0.9, 1.0).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims and/or aspects included herein, as permitted by applicable law.

Exemplary Embodiments of the Invention

To better illustrate the invention described herein, a non-limiting list of exemplary embodiments and features of the invention is provided here. These embodiments are more fully described in, and additional embodiments, features, and advantages of the invention will be apparent from, the description of the invention provided herein.

The following embodiments relate to compositions for modulating NK cell activity in a patient in need thereof:
1. A method of modulating NK cell activity in a patient in need thereof, comprising administering to the patient an antibody that binds at least one human inhibitory KIR at a dose in the range from about 0.0003 to about 3 mg/kg.
2. The method of embodiment 1, wherein the dose is in the range from about 0.075 to about 3 mg/kg.
3. The method of embodiment 2, wherein the dose is selected from about 0.0003, about 0.003, about 0.015, about 0.075, about 0.3, about 1, and about 3 mg/kg.
4. The method of embodiment 1, comprising repeating the administration at least once.
5. The method of embodiment 1, wherein the administration is repeated with a dosing frequency in the range of 3 times per day to once per 2 months.
6. The method of any one of the preceding embodiments, wherein the dose is administered at least 3 times.
7. The method of embodiment 14, wherein the dose is administered at least 6 times.
8. The method of any one of the preceding embodiments, wherein the antibody is administered intravenously.
9. The method of any of the preceding embodiments, wherein binding of the antibody to an inhibitory KIR on the surface of an NK cell potentiates the cytotoxic activity of the NK cell
10. The method of any of the preceding embodiments, wherein the antibody is a cross-reactive anti-KIR antibody.

11. The method of any of the preceding embodiments, wherein the antibody has one or more properties of
   (a) a high affinity Kd from about 2 to about 6 ng/ml;
   (b) a low affinity Kd from about 10 to about 30 ng/ml;
   (c) a clearance of from about 0.25 to about 0.75 ml/h/kg; and
   (d) a volume of distribution of from about 50 ml/kg to about 175 ml/kg.
12. The method of embodiment 11, wherein the antibody has all of properties (a) to (d).
13. The method of any of the preceding embodiments, wherein the antibody comprises the variable heavy (SEQ ID NO:3) and variable light (SEQ ID NO:2) region sequences of antibody 1-7F9.
14. The method of any of the preceding embodiments, wherein the antibody comprises a heavy chain comprising the sequence of SEQ ID NO:1.
15. The method of any one of the preceding embodiments, wherein the patient has increased CD107a levels on NK cells in a blood sample taken from the patient 24 hrs after the first dose.
16. The method of any of the preceding claims, wherein the does not have increased CD107a levels on T cells in the blood sample.
17. The method of any of the preceding embodiments, resulting in at least about 50% KIR occupancy on NK cells.
18. The method of any of the preceding embodiments, resulting in at least about 90% KIR occupancy on NK cells.

The following embodiments relate to methods of treating cancer in a patient, and related articles:

1. A method of treating cancer in a patient, comprising administering an anti-KIR antibody at a dose and a dosing frequency achieving at least about 95% KIR occupancy on NK cells in blood for at least about three months.
2. The method of embodiment 1, wherein the dose is in the range from about 0.003 to about 3 mg/kg.
3. The method of embodiment 1, wherein the dose is in the range from about 0.075 to about 3 mg/kg.
4. The method of embodiment 2, wherein the dose is selected from about 0.0003, about 0.003, about 0.015, about 0.075, about 0.3, about 1, and about 3 mg/kg.
5. The method of embodiment 1, wherein the dosing frequency is in the range of once per day to once per 2 months.
6. The method of embodiment 5, wherein the dosing frequency is in the range from about once per week to about once per 2 months.
7. The method of embodiment 6, wherein the dosing frequency is about once per month.
8. The method of embodiment 5, wherein the dosing frequency is selected from about three times, about twice, and about once per day; about five times, about four times, about three times, and about twice per week; and about once every two, four, and six weeks.
9. The method of embodiment 1, wherein a dose of from about 0.075 to about 0.3 mg/kg is administered from about 2 times per week to about once per month.
10. The method of embodiment 1, wherein a dose of from about 0.3 to about 1 mg/kg is administered from about once to about twice per month.
11. The method of embodiment 1, wherein a dose of from about 1 to about 3 mg/kg is administered from about once per month to about once every 2 months.
12. The method of any of embodiments 10 and 11, wherein the dosing frequency is about once per month.
13. The method of embodiment 1, wherein the dose and dosing frequency are selected from any one of the following combinations:

| Dose (mg/kg) | Dosing regimen |
|---|---|
| About 0.003 | 1-2 times per day |
| About 0.015 | 3-5 times per week |
| About 0.075 | 1-2 times per week |
| About 0.3 | 1-2 times per month |
| About 1 | About 1 time per month |
| About 3 | 1-2 times per 2-month period |

14. The method of any one of the preceding embodiments, wherein the dose is administered at least 3 times.
15. The method of embodiment 14, wherein the dose is administered at least 6 times.
16. The method of any of the preceding embodiments, comprising administering an anti-KIR antibody at a dose and a dosing frequency achieving at least about 95% KIR occupancy on NK cells in blood for at least about six months.
17. The method of any of the preceding embodiments, wherein the cancer is acute myeloid leukaemia (AML), chronic myeloid leukaemia (CML), multiple myeloma (MMy), non-Hodgkin's lymphoma (NHL), colorectal cancer, renal cancer, ovarian cancer, lung cancer, breast cancer, or malignant melanoma.
18. The method of any one of the preceding embodiments, wherein the antibody is administered intravenously.
19. The method of any of the preceding embodiments, wherein binding of the antibody to an inhibitory KIR on the surface of an NK cell potentiates the cytotoxic activity of the NK cell
20. The method of any of the preceding embodiments, wherein the antibody is a cross-reactive anti-KIR antibody.
21. The method of any of the preceding embodiments, wherein the antibody has one or more properties of
   (a) a high affinity Kd from about 2 to about 6 ng/ml;
   (b) a low affinity Kd from about 10 to about 30 ng/ml;
   (c) a clearance of from about 0.25 to about 0.75 ml/h/kg; and
   (d) a volume of distribution of from about 50 ml/kg to about 175 ml/kg.
22. The method of embodiment 21, wherein the antibody has all of properties (a) to (d).
23. The method of any of the preceding embodiments, wherein the antibody comprises the variable heavy (SEQ ID NO:3) and variable light (SEQ ID NO:2) region sequences of antibody 1-7F9.
24. The method of any of the preceding embodiments, wherein the antibody comprises a heavy chain comprising the sequence of SEQ ID NO:1.
25. The method of any one of the preceding embodiments, wherein the patient has increased CD107a levels on NK cells in a blood sample taken about 24 hrs after the first dose.
26. The method of any of the preceding claims, wherein the does not have increased CD107a levels on T cells in the blood sample.
27. The method of any of the preceding embodiments, wherein the patient suffers from AML and wherein the levels of Wilms' tumour gene 1 transcript in blood and/or bone marrow are reduced after one or more doses of anti-KIR antibody.

28. The method of any of the preceding embodiments, wherein the patient suffers from MMy and wherein the levels of M-protein in urine are reduced after one or more doses of anti-KIR antibody.

The following embodiments describe exemplary articles of manufacture (e.g., kits) according to the invention:

1. An article of manufacture comprising:
   (a) a container comprising an anti-KIR antibody; and
   (b) a package insert with instructions for treating cancer in a patient, wherein the instructions indicate that a dose of the anti-KIR antibody of about 0.003 to about 3 mg/kg is administered to the patient at a frequency of from about once per day to about once every 2 months.
2. The article of embodiment 1, wherein the dose is from about 0.075 to about 0.3 mg/kg and the dosing frequency is from about 2 times per week to about once per month.
3. The article of embodiment 1, wherein the dose is from about 0.3 to about 1 mg/kg and the dosing frequency is from about 1 to about 2 times per month.
4. The article of embodiment 1, wherein the dose is from about 1 mg/kg to about 3 mg/kg and the dosing frequency is from about once per month to about once every 2 months.
5. The article of any of embodiments 30 and 31, wherein the dosing frequency is about once a month.
6. The article of embodiment 1, wherein the dose and dosing frequency are selected from any one of the following combinations:

| Dose (mg/kg) | Dosing regimen |
| --- | --- |
| About 0.003 | 1-2 times per day |
| About 0.015 | 3-5 times per week |
| About 0.075 | 1-2 times per week |
| About 0.3 | 1-2 times per month |
| About 1 | About 1 time per month |
| About 3 | 1-2 times per 2-month period |

7. The article of embodiment 1, further comprising a container comprising a second medicament, wherein the package insert further comprises instructions for treating the patient with the second medicament.
8. The article of embodiment 7, wherein the second medicament is a an immunomodulatory agent, a hormonal agent, a chemotherapeutic agent, an anti-angiogenic agent, an apoptotic agent, a second antibody that binds to an inhibitory KIR, an anti-infective agent, a targeting agent, and an anti-CD20 antibody.

The following embodiments of the invention relate to pharmaceutical formulations of anti-KIR antibodies.

1. A pharmaceutically acceptable and active formulation comprising (a) about 0.05 mg/mL to about 10 mg/mL of an IgG4 antibody; (b) about 10-50 mM sodium phosphate; (c) about 160-250 mM sucrose or about 100 mM NaCl; and (d) polysorbate 80, at a pH of about 7.
2. The formulation of embodiment 1, wherein the antibody is a neutralizing anti-KIR antibody.
3. The formulation of embodiment 2, wherein the antibody is a cross-reactive anti-KIR antibody.
4. The formulation of embodiment 3, wherein the antibody comprises a heavy chain sequence according to SEQ ID NO:3.
5. The formulation of embodiment 4, wherein the antibody comprises a light chain sequence according to SEQ ID NO:2.
6. The formulation of embodiment 5, wherein the heavy chain sequence comprises SEQ ID NO:1.
7. The formulation of any of embodiments 1-3, wherein the concentration of the IgG4 antibody molecule is about 1-10 mg/ml.
8. The formulation of embodiment 7, wherein the concentration of IgG4 antibody is 10 mg/ml.
9. The formulation of any of embodiments 1 to 8, comprising about 20-50 mM sodium phosphate, about 220-250 mM sucrose, and about 0.001% polysorbate 80.
10. The formulation of embodiment 9, comprising about 20 mM sodium phosphate and about 220 mM sucrose.
11. A pharmaceutically acceptable and active formulation comprising (a) about 0.05 mg/mL to about 10 mg/mL of an IgG4 antibody molecule comprising a heavy chain according to SEQ ID NO:1 and a light chain comprising a light chain variable region according to SEQ ID NO:2; (b) about 50 mM sodium phosphate; (c) about 250 mM sucrose; and (d) about 0.001% polysorbate 80, at a pH of about 7.
12. A pharmaceutically acceptable and active formulation comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 50 mM sodium phosphate; (c) about 250 mM sucrose or about 100 mM sodium chloride; and (d) about 0.001% polysorbate 80, wherein the formulation has a pH of about 7.
13. A pharmaceutically acceptable and active formulation comprising (a) about 0.05 mg/mL to about 10 mg/mL of an IgG4 antibody molecule comprising a heavy chain according to SEQ ID NO:1 and a light chain comprising a light chain variable region according to SEQ ID NO:2; (b) about 20 mM sodium phosphate; (c) about 220 mM sucrose; and (d) about 0.001% polysorbate 80, at a pH of about 7.
14. A pharmaceutically acceptable and active formulation comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 20 mM sodium phosphate; (c) about 220 mM sucrose or about 100 mM sodium chloride; and (d) about 0.001% polysorbate 80, wherein the formulation has a pH of about 7.
15. The formulation of any of embodiments 1-14, wherein the antibody is 1-F79.
16. The formulation according to any one of embodiments 1-15, wherein the concentration of the antibody in the formulation is about 10 mg/mL.
17. The formulation according to any one of embodiments 1-15, wherein the concentration of the antibody in the formulation is about 0.05 mg/mL.
18. A pharmaceutically acceptable and active formulation prepared from a mixture of ingredients comprising (a) an amount of an IgG4 antibody molecule comprising a heavy chain comprising a heavy chain variable region according to SEQ ID NO:3 and a light chain comprising a light chain variable region according to SEQ ID NO:2 such that the concentration of antibody in the formulation is about 10 mg/mL; (b) about 8.4 mg/mL sodium phosphate dibasic (heptahydrate); (c) about 2.6 mg/mL sodium phosphate monobasic; (d) about 85 mg/mL sucrose; and (e) about 0.01 mg/mL polysorbate 80, wherein the formulation has a pH of about 7.

19. The formulation of embodiment 18, wherein the antibody comprises a heavy chain according to SEQ ID NO:1.

20. The formulation of embodiment 19, wherein the antibody is 1-F79.

21. The formulation of any one of embodiments 1-20, wherein the formulation has an impurity content of less than about 10% for up to about 1 month of storage at about 5° C.

22. The formulation of embodiment 21, wherein the formulation has a high molecular weight protein impurity content of less than about 5% for up to about 3 months of storage at about 5° C.

23. A pharmaceutically acceptable and active formulation comprising (a) about 0.05 mg/mL to about 10 mg/mL of an IgG4 antibody molecule comprising a heavy chain comprising a heavy chain variable region according to SEQ ID NO:3 and a light chain comprising a light chain variable region according to SEQ ID NO:2; (b) about 5-20 mM sodium phosphate; (c) about 180 to about 250 mM sucrose; and (d) about 0.001-0.1% polysorbate 80, wherein the formulation has a pH of about 7.

24. The formulation according to embodiment 21, wherein the formulation comprises about 200 mM sucrose.

25. The formulation of embodiment 23 or embodiment 24, wherein the formulation has an impurity content of less than about 10% for up to about 1 month of storage at about 5° C.

26. The formulation of any one of embodiments 23-25, wherein the formulation has a high molecular weight protein impurity content of less than about 5% for up to about 3 months of storage at about 5° C.

27. The formulation of any one of embodiments 23-26, wherein the formulation is isotonic.

28. The formulation of any one of embodiments 23-27, wherein the concentration of the antibody in the formulation is about 10 mg/mL.

29. The formulation of any one of embodiments 23-77, wherein the concentration of the antibody in the formulation is about 0.05 mg/mL.

30. The formulation of any one of embodiments 23-27, wherein the concentration of the antibody in the formulation is about 0.1 mg/mL.

31. The formulation of any one of embodiments 23-27, wherein the concentration of the antibody in the formulation is about 1 mg/mL.

32. A method of preparing a pharmaceutically acceptable formulation for human administration by intravenous injection comprising storing a concentrated formulation according to any one of embodiments 1-20 at a temperature of from about 5° C. and diluting the concentrated formulation in a solution comprising components (b)-(d) of embodiment 1 (but lacking any antibody) to produce an administration-ready (diluted) product, and storing the administration-ready product at a temperature of from about 5° C. for up to about 24 hours before administration.

33. The method of embodiment 32, wherein the concentrated product has an antibody concentration of about 1 mg/mL to about 10 mg/mL and the dilute product has an antibody concentration of about 0.05 mg/mL.

34. A method of preparing a pharmaceutically acceptable formulation for human administration by intravenous injection comprising storing a concentrated formulation according to any one of embodiments 21-31 at a temperature of from about 5° C. and diluting the concentrated formulation in a sterile isotonic saline solution to produce an administration-ready (diluted) product, and storing the administration-ready product at a temperature of from about 5° C. for up to about 24 hours before administration.

35. The method of embodiment 34, wherein the concentrated product has an antibody concentration of about 1 mg/mL to about 10 mg/mL and the dilute product has an antibody concentration of about 0.05 mg/mL.

36. A pharmaceutical product comprising a storage container comprising a formulation according to any one of embodiments 1-22 in a volume of about 3 mL to about 30 mL.

37. The product of embodiment 36, wherein the container comprises about 5 mL or about 10 mL of the formulation.

38. A pharmaceutical product comprising a storage container comprising a formulation according to any one of embodiments 23-31 in a volume of about 3 mL to about 30 mL.

39. The product of embodiment 38, wherein the container comprises about 5 mL or about 10 mL of the formulation.

40. A method of potentiating NK cell activity in a patient in need thereof comprising administering to the patient a formulation according to any one of embodiments 1-31 in an antibody dosage of about 0.0003 mg/kg (patient weight) to about 3 mg/kg.

41. The method of embodiment 40, wherein the dosage is about 0.001 mg/kg to about 3 mg/kg.

42. The method of embodiment 40 or embodiment 41, wherein the patient is a patient diagnosed with a cancer.

43. The method of embodiment 42, wherein the patient is a patient diagnosed with acute myeloid leukaemia.

44. The method of embodiment 42, wherein the patient is a patient diagnosed with chronic myeloid leukaemia.

45. The method of embodiment 42, wherein the patient is a patient diagnosed with multiple myeloma.

46. The method of embodiment 42, wherein the patient is a patient diagnosed with non-Hodgkin's lymphoma.

47. The method of embodiment 42, wherein the patient is a patient diagnosed with colorectal cancer.

48. The method of embodiment 42, wherein the patient is a patient diagnosed with renal cancer.

49. The method of embodiment 42, wherein the patient is a patient diagnosed with ovarian cancer.

50. The method of embodiment 42, wherein the patient is a patient diagnosed with lung cancer.

51. The method of embodiment 42, wherein the patient is a patient diagnosed with breast cancer.

52. The method of embodiment 42, wherein the patient is a patient diagnosed with malignant melanoma.

53. The method of embodiment 40 or 41, wherein the patient is a patient diagnosed with an infectious disease.

54. The method of any one of embodiments 40-53, wherein the method comprises administering one or more additional dosages of about 0.0003 mg/kg to about 3 mg/kg to the patient at least about 6 hours after the previous administration.

55. Use of a formulation according to any one of embodiments 1-31 in the preparation of a medicament.

56. Use of a formulation according to any one of embodiments 1-31 for the preparation of a medicament for the treatment of cancer or an infectious disease.

57. Use of a formulation according to any one of embodiments 1-31 in an amount that provides an antibody dosage of about 0.0003 mg/kg to about 3 mg/kg as a medicament for the treatment of cancer.

58. A formulation according to any one of embodiments 1-31 for use in the treatment of cancer or an infectious disease.

59. A formulation according to any one of embodiments 1-31 for use in the treatment of cancer.

What is claimed is:

1. An isolated anti-KIR antibody or antigen-binding fragment thereof comprising a heavy chain having the amino acid sequence set forth in SEQ ID NO:1 and a light chain variable region having the amino acid sequence set forth in SEQ ID NO:2.

2. A pharmaceutical composition comprising an isolated anti-KIR antibody or antigen-binding fragment thereof comprising a heavy chain having the amino acid sequence set forth in SEQ ID NO:1 and a light chain variable region having the amino acid sequence set forth in SEQ ID NO:2.

3. The composition of claim 2, which includes another therapeutic agent that is not an anti-KIR antibody.

4. The composition of claim 2, which comprises a pH of about 7.

5. The composition of claim 2, which comprises a dosage of said anti-KIR antibody of about 0.0003 mg (antibody)/kg (patient weight) to about 3 mg/kg.

6. The composition of claim 2, which comprises a dosage of said anti-KIR antibody of about 0.015 to about 3 mg/kg, about 0.075 mg to about 3 mg/kg, about 0.3 mg/kg to about 3 mg/kg, about 1 mg/kg to about 3 mg/kg, or any of about 0.0003 mg/kg, about 0.003 mg/kg, about 0.015 mg/kg, about 0.075 mg/kg, about 0.3 mg/kg, about 1 mg/kg, or about 3 mg/kg.

7. The composition of claim 2, which comprises (a) about 0.05 mg/mL to about 10 mg/mL of said anti-KIR antibody which comprises an IgG4 antibody; (b) about 10-50 mM sodium phosphate; (c) about 160-250 mM sucrose or about 100 mM NaCl; and (d) polysorbate 80, at a pH of about 7.

8. The composition of claim 2, which comprises about 0.05 mg/mL to about 10 mg/mL of said anti-KIR antibody which comprises an IgG4 antibody.

9. The composition of claim 2, which comprises (a) about 0.05 mg/mL to about 10 mg/mL of said anti-KIR antibody which comprises an IgG4 antibody; (b) about 5-20 mM sodium phosphate, about 5 mM sodium phosphate, about 10 mM sodium phosphate, about 15 mM sodium phosphate, or about 20 mM sodium phosphate; (c) about 180 to about 250 mM sucrose; and (d) about 0.001% or about 0.01-0.1% polysorbate 80, wherein the formulation has a pH of about 7.

10. The composition of claim 2, which comprises less than about 35 mM sodium phosphate.

11. The composition of claim 2, which comprises more than about 0.005% polysorbate 80.

12. The composition of claim 2, which is isotonic.

* * * * *

SEQUENCE LISTING

<160> NUMBER OF SEQ ID NOS: 7

<210> SEQ ID NO 1
<211> LENGTH: 469
<212> TYPE: PRT
<213> ORGANISM: Homo sapiens
<220> FEATURE:
<221> NAME/KEY: SIGNAL
<222> LOCATION: (1)..(8)

<400> SEQUENCE: 1

```
Met Asp Trp Thr Trp Arg Phe Leu Phe Val Val Ala Ala Ser Thr Gly
  1               5                  10                  15

Val Gln Ser Gln Val Gln Leu Val Gln Ser Gly Ala Glu Val Lys Lys
             20                  25                  30

Pro Gly Ser Ser Val Lys Val Ser Cys Lys Ala Ser Gly Gly Thr Phe
         35                  40                  45

Ser Phe Tyr Ala Ile Ser Trp Val Arg Gln Ala Pro Gly Gln Gly Leu
     50                  55                  60

Glu Trp Met Gly Gly Phe Ile Pro Ile Phe Gly Ala Ala Asn Tyr Ala
 65                  70                  75                  80

Gln Lys Phe Gln Gly Arg Val Thr Ile Thr Ala Asp Glu Ser Thr Ser
                 85                  90                  95

Thr Ala Tyr Met Glu Leu Ser Ser Leu Arg Ser Asp Asp Thr Ala Val
            100                 105                 110

Tyr Tyr Cys Ala Arg Ile Pro Ser Gly Ser Tyr Tyr Tyr Asp Tyr Asp
        115                 120                 125

Met Asp Val Trp Gly Gln Gly Thr Thr Val Thr Val Ser Ser Ala Ser
130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Lys Thr Tyr Thr
    210                 215                 220

Cys Asn Val Asp His Lys Pro Ser Asn Thr Lys Val Asp Lys Arg Val
225                 230                 235                 240

Glu Ser Lys Tyr Gly Pro Pro Cys Pro Pro Cys Pro Ala Pro Glu Phe
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350
```

```
Ser Ile Glu Lys Thr Ile Ser Lys Ala Lys Gly Gln Pro Arg Glu Pro
            355                 360                 365

Gln Val Tyr Thr Leu Pro Pro Ser Gln Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Leu Gly Lys
465

<210> SEQ ID NO 2
<211> LENGTH: 109
<212> TYPE: PRT
<213> ORGANISM: Homo sapiens

<400> SEQUENCE: 2

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105

<210> SEQ ID NO 3
<211> LENGTH: 123
<212> TYPE: PRT
<213> ORGANISM: Homo sapiens

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95
```

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 4
<211> LENGTH: 30
<212> TYPE: DNA
<213> ORGANISM: artificial
<220> FEATURE:
<223> OTHER INFORMATION: Primer

<400> SEQUENCE: 4
cccccatgcc caccatgccc agcacctgag                                      30

<210> SEQ ID NO 5
<211> LENGTH: 30
<212> TYPE: DNA
<213> ORGANISM: artificial
<220> FEATURE:
<223> OTHER INFORMATION: Primer

<400> SEQUENCE: 5
ctcaggtgct gggcatggtg ggcatggggg                                      30

<210> SEQ ID NO 6
<211> LENGTH: 1410
<212> TYPE: DNA
<213> ORGANISM: Artificial
<220> FEATURE:
<223> OTHER INFORMATION: Mutant

<400> SEQUENCE: 6
atggactgga cctggaggtt cctctttgtg gtggcagcat ctacaggtgt ccagtcccag      60
gtccagctgg tgcagtctgg ggctgaggtg aagaagcctg gtcctcggt gaaggtctcc     120 tgcaaggctt ctggaggcac cttcagtttc tatgctatca gctgggtgcg acaggccct    180 ggacaagggc ttgagtggat gggagggttc atccctatct ttggtgcagc aaactacgca    240
cagaagttcc agggcagagt cacgattacc gcggacgaat ccacgagcac agcctacatg    300
gaactgagca gcctgagatc tgacgacacg gccgtgtatt actgtgcgag aatccctagt    360
gggagctact actacgacta cgatatggac gtctggggcc aagggaccac ggtcaccgtc    420
tcctcagcta gcaccaaggg cccatccgtc ttccccctgg cgccctgctc caggagcacc    480
tccgagagca cagccgccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacg    660
aagacctaca cctgcaacgt agatcacaag cccagcaaca ccaaggtgga caagagagtt    720
gagtccaaat atggtccccc atgcccacca tgcccagcac ctgagttcct ggggggacca    780
tcagtcttcc tgttccccc aaaacccaag gacactctca tgatctcccg gacccctgag    840
gtcacgtgcg tggtggtgga cgtgagccag gaagacccccg aggtccagtt caactggtac    900
gtggatggcg tggaggtgca taatgccaag acaaagccgc gggaggagca gttcaacagc    960
acgtaccgtg tggtcagcgt cctcaccgtc ctgcaccagg actggctgaa cggcaaggag   1020
tacaagtgca aggtctccaa caaaggcctc ccgtcctcca tcgagaaaac catctccaaa   1080
gccaaagggc agccccgaga gccacaggtg tacaccctgc ccccatccca ggaggagatg   1140
accaagaacc aggtcagcct gacctgcctg gtcaaaggct tctaccccag cgacatcgcc   1200

```
gtggagtggg agagcaatgg gcagccggag aacaactaca agaccacgcc tcccgtgctg    1260
gactccgacg gctccttctt cctctacagc aggctaaccg tggacaagag caggtggcag    1320
gaggggaatg tcttctcatg ctccgtgatg catgaggctc tgcacaacca ctacacacag    1380
aagagcctct ccctgtctct gggtaaatga                                    1410

<210> SEQ ID NO 7
<211> LENGTH: 1410
<212> TYPE: DNA
<213> ORGANISM: Artificial
<220> FEATURE:
<223> OTHER INFORMATION: Mutant

<400> SEQUENCE: 7
tacctgacct ggacctccaa ggagaaacac caccgtcgta gatgtccaca ggtcagggtc      60
caggtcgacc acgtcagacc ccgactccac ttcttcggac ccaggagcca cttccagagg     120
acgttccgaa gacctccgtg gaagtcaaag atacgatagt cgacccacgc tgtccgggga     180
cctgttcccg aactcaccta ccctcccaag tagggataga aaccacgtcg tttgatgcgt     240
gtcttcaagg tcccgtctca gtgctaatgg cgcctgctta ggtgctcgtg tcggatgtac     300
cttgactcgt cggactctag actgctgtgc cggcacataa tgacacgctc ttagggatca     360
ccctcgatga tgatgctgat gctatacctg cagaccccgg ttccctggtg ccagtggcag     420
aggagtcgat cgtggttccc gggtaggcag aaggggggacc gcgggacgag gtcctcgtgg    480
aggctctcgt gtcggcggga cccgacggac cagttcctga tgaagggggct tggccactgc    540 cacagcacct tgagtccgcg ggactggtcg ccgcacgtgt ggaagggccg acaggatgtc     600
aggagtcctg agatgaggga gtcgtcgcac cactggcacg ggaggtcgtc gaacccgtgc     660
ttctggatgt ggacgttgca tctagtgttc gggtcgttgt ggttccacct gttctctcaa     720
ctcaggttta taccagggggg tacgggtggt acgggtcgtg gactcaagga ccccctggt     780 agtcagaagg acaagggggg ttttgggttc ctgtgagagt actagagggc ctggggactc     840
cagtgcacgc accaccacct gcactcggtc cttctggggc tccaggtcaa gttgaccatg     900
cacctaccgc acctccacgt attacggttc tgtttcggcg ccctcctcgt caagttgtcg     960
tgcatggcac accagtcgca ggagtggcag gacgtggtcc tgaccgactt gccgttcctc    1020
atgttcacgt tccagaggtt gtttccggag ggcaggaggt agctcttttg gtagaggttt    1080
cggtttcccg tcggggctct cggtgtccac atgtgggacg ggggtagggt cctcctctac    1140
tggttcttgg tccagtcgga ctggacggac cagtttccga agatggggtc gctgtagcgg    1200
cacctcaccc tctcgttacc cgtcggcctc ttgttgatgt tctggtgcgg agggcacgac    1260
ctgaggctgc cgaggaagaa ggagatgtcg tccgattggc acctgttctc gtccaccgtc    1320 ctcccttac agaagagtac gaggcactac gtactccgag acgtgttggt gatgtgtgtc    1380
ttctcggaga gggacagaga cccatttact                                    1410
```